United States Patent
Chien

(10) Patent No.: US 11,121,513 B2
(45) Date of Patent: *Sep. 14, 2021

(54) LED NIGHT LIGHT OR COVER LIGHT HAS MULTIPLE FUNCTIONS

(71) Applicant: Tseng-Lu Chien, Walnut, CA (US)

(72) Inventor: Tseng-Lu Chien, Walnut, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/690,582

(22) Filed: Nov. 21, 2019

(65) Prior Publication Data

US 2020/0153187 A1  May 14, 2020

Related U.S. Application Data

(60) Division of application No. 14/817,675, filed on Aug. 4, 2015, now Pat. No. 10,505,326, which is a continuation-in-part of application No. 13/910,295, filed on Jun. 5, 2013, now Pat. No. 9,732,921, application No. 16/690,582, which is a continuation-in-part of application No. 16/686,525, (Continued)

(51) Int. Cl.
| | |
|---|---|
| F21V 23/04 | (2006.01) |
| H01R 27/02 | (2006.01) |
| H01R 13/66 | (2006.01) |
| H01R 13/70 | (2006.01) |
| H01R 13/717 | (2006.01) |
| H01R 13/73 | (2006.01) |
| A61L 9/03 | (2006.01) |
| H02G 3/14 | (2006.01) |
| F21S 8/00 | (2006.01) |
| H02G 3/18 | (2006.01) |
| F21V 33/00 | (2006.01) |
| H01R 24/76 | (2011.01) |
| F21Y 115/10 | (2016.01) |

(52) U.S. Cl.
CPC ............ *H01R 27/02* (2013.01); *A61L 9/03* (2013.01); *F21S 8/033* (2013.01); *F21V 23/0442* (2013.01); *F21V 33/00* (2013.01); *H01R 13/665* (2013.01); *H01R 13/70* (2013.01); *H01R 13/7175* (2013.01); *H01R 13/73* (2013.01); *H02G 3/14* (2013.01); *H02G 3/18* (2013.01); *A61L 2209/111* (2013.01); *A61L 2209/12* (2013.01); *A61L 2209/133* (2013.01); *F21Y 2115/10* (2016.08); *H01R 24/76* (2013.01)

(58) Field of Classification Search
None
See application file for complete search history.

(56) References Cited

U.S. PATENT DOCUMENTS

| 5,556,192 A * | 9/1996 | Wang | F21S 8/035 |
| | | | 362/276 |
| 6,431,719 B1 * | 8/2002 | Lau | F21V 23/0442 |
| | | | 362/95 |

(Continued)

*Primary Examiner* — Elmito Breval
(74) *Attorney, Agent, or Firm* — Bacon & Thomas, PLLC

(57) ABSTRACT

The LED night light or cover light has multiple Functions has built-in LED(s) for pre-determined illumination shown on housing, window, hole(s) of night or cover light which connect by prong to an existing wall inner-kit's receptacle to get AC power source to circuit(s) for predetermined at least LED(s) illumination functions. The night or cover light further incorporate with at least one USB charger, Outlet(s), IC, photo sensor, motion sensor, power fail sensor, surge or other protection system.

18 Claims, 9 Drawing Sheets

Geometric Constrution
LED night light

Related U.S. Application Data filed on Nov. 18, 2019, which is a division of application No. 13/117,227, filed on May 27, 2011, now abandoned, application No. 16/690,582, which is a continuation-in-part of application No. 16/298,110, filed on Mar. 11, 2019, now Pat. No. 10,753,561, which is a continuation of application No. 14/739,397, filed on Jun. 15, 2015, now Pat. No. 10,184,624, which is a continuation of application No. 11/806,285, filed on May 31, 2007, said application No. 16/298,110 is a continuation-in-part of application No. 11/498,874, filed on Aug. 4, 2006, now abandoned, which is a continuation of application No. 10/954,189, filed on Oct. 1, 2004, now abandoned, application No. 16/690,582, which is a continuation-in-part of application No. 14/739,397, which is a continuation-in-part of application No. 11/806,284, filed on May 31, 2007, now Pat. No. 7,632,004, application No. 16/690,582, which is a continuation-in-part of application No. 11/806,285, filed on May 31, 2007, and a continuation-in-part of application No. 16/285,631, filed on Feb. 26, 2019, now Pat. No. 10,907,784, and a continuation-in-part of application No. 16/242,762, filed on Jan. 8, 2019, and a continuation-in-part of application No. 14/739,666, filed on Jun. 15, 2015, now Pat. No. 10,487,999, and a continuation-in-part of application No. 14/739,499, filed on Jun. 15, 2015, now Pat. No. 10,508,784.

(56) References Cited

U.S. PATENT DOCUMENTS

| | | | | |
|---|---|---|---|---|
| 6,478,440 B1 * | 11/2002 | Jaworski | | A01M 1/04 362/253 |
| 6,540,554 B2 | 4/2003 | McCarthy | | |
| 6,741,442 B1 * | 5/2004 | McNally | | G06F 1/206 361/166 |
| 6,862,403 B2 * | 3/2005 | Pedrotti | | A01M 1/2072 392/392 |
| 3,297,886 A1 | 1/2007 | Danner | | |
| 7,318,653 B2 | 1/2008 | Chien | | |
| 7,338,328 B2 | 3/2008 | Krieger | | |
| 7,862,350 B2 | 1/2011 | Richter | | |
| 7,997,925 B2 | 8/2011 | Lam | | |
| 8,439,692 B1 | 5/2013 | Oddsen | | |
| 8,758,031 B2 | 6/2014 | Cheng | | |
| 2002/0172512 A1 * | 11/2002 | Stathakis | | A61L 9/03 392/395 |
| 2003/0137258 A1 * | 7/2003 | Piepgras | | H05B 45/20 315/291 |
| 2004/0032497 A1 * | 2/2004 | Ying | | H04N 7/142 348/207.1 |
| 2004/0085030 A1 * | 5/2004 | Laflamme | | F21V 23/045 315/291 |
| 2004/0090774 A1 * | 5/2004 | Hsueh | | F21V 23/0442 362/183 |
| 2004/0145890 A1 * | 7/2004 | Liao | | H01R 31/065 362/183 |
| 2004/0207334 A1 * | 10/2004 | Lin | | H05B 45/395 315/185 S |
| 2005/0180137 A1 * | 8/2005 | Hsu | | F21V 3/02 362/249.01 |
| 2008/0012423 A1 | 1/2008 | Mimran | | |
| 2008/0140565 A1 | 6/2008 | Debenedetti et al. | | |
| 2008/0304289 A1 * | 12/2008 | Chien | | H04N 5/2252 362/641 |
| 2009/0315509 A1 | 12/2009 | Wu | | |
| 2012/0275763 A1 | 11/2012 | Quezada | | |
| 2012/0292991 A1 | 11/2012 | Dodal | | |
| 2013/0280956 A1 * | 10/2013 | Cheng | | H02G 3/12 439/620.15 |

* cited by examiner

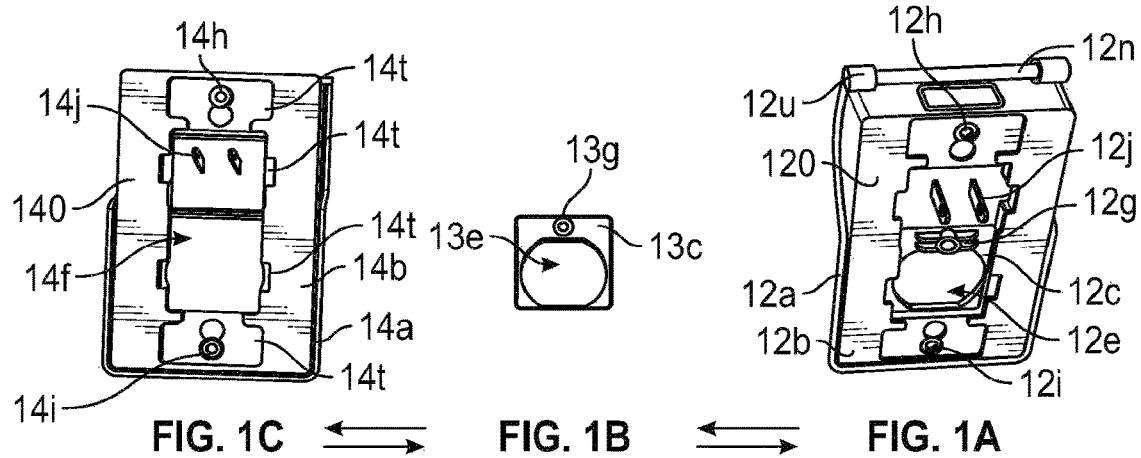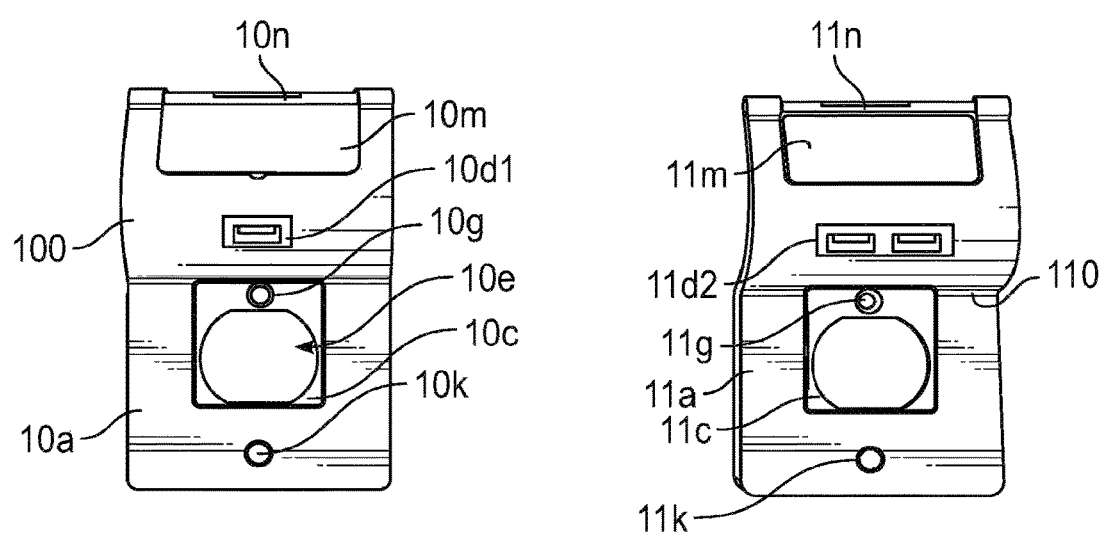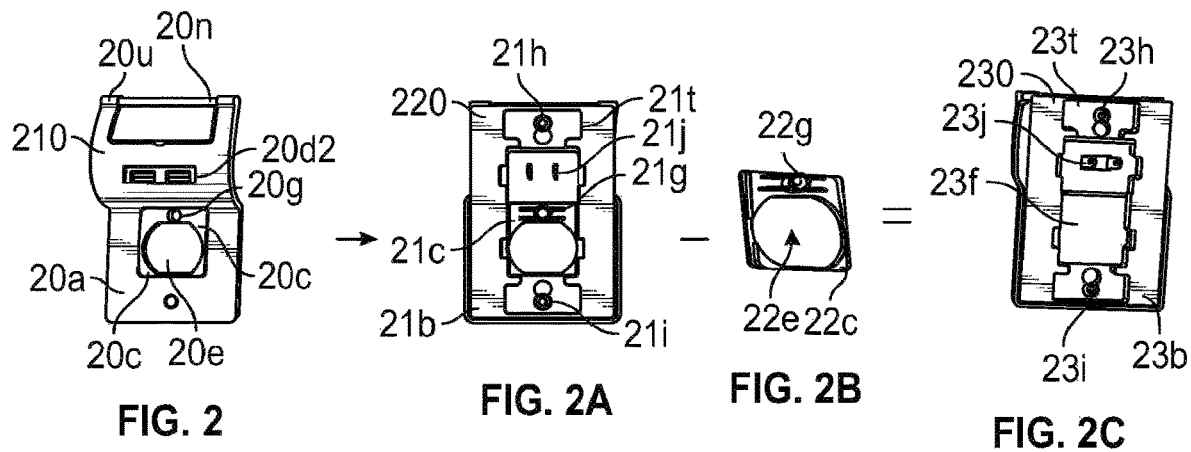

FIG. 10
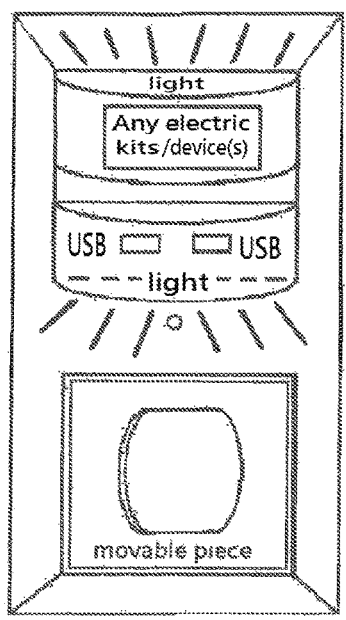
FIG. 11
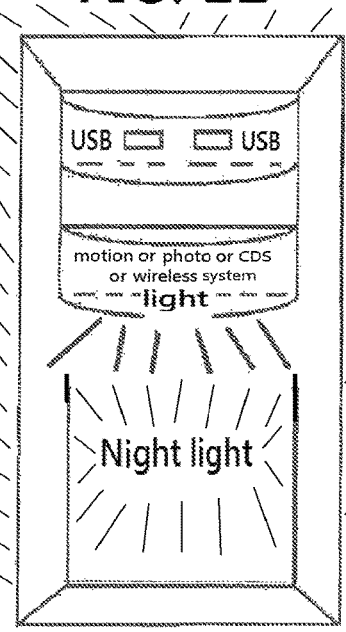
FIG. 12
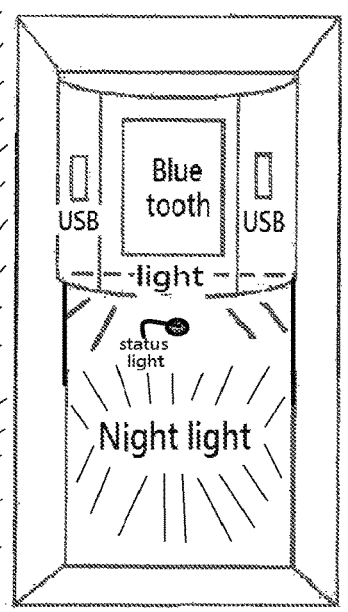
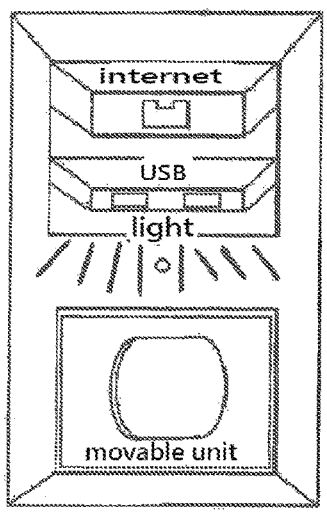
FIG. 13
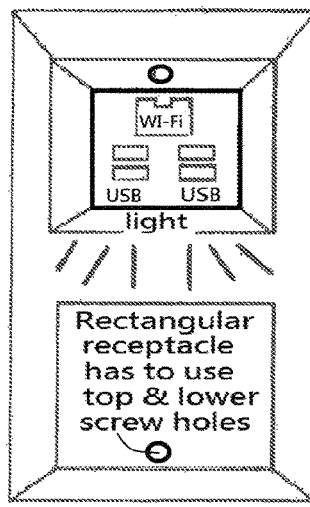
FIG. 14
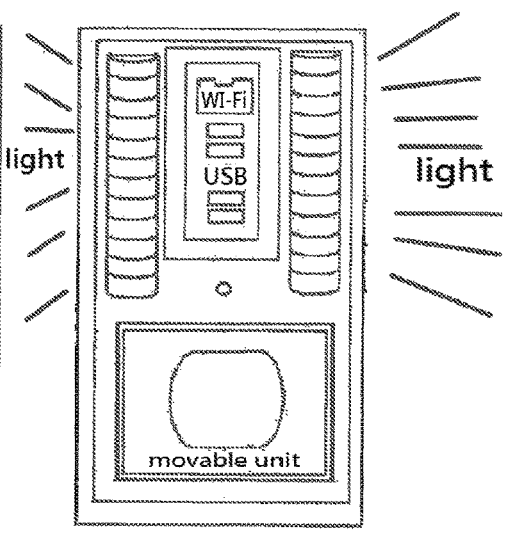
FIG. 15

LED Plug in night light or colver plate light has built-in at least one outlet(s), USB charger, Wi-Fi, ZigBee, Z-way, router system, or other electric device(s)

LED NIGHT LIGHT OR COVER LIGHT HAS MULTIPLE FUNCTIONS

RELATED U.S. PATENT DOCUMENTS

The current invention is
Division file case of
(#VVV-1) U.S. application Ser. No. 14/817,675 filed on Aug. 4, 2015 now allowed,
Which is Division of
(#VVV-2013) U.S. application Ser. No. 13/910,295 filed on Jun. 5, 2013 now is U.S. Pat. No. 9,732,921,
Which is Continue of
(#FFF-1D) U.S. application Ser. No. 16/686,525 filed on Nov. 18, 2019,
Which is Division of
(#FFF-2011) U.S. application Ser. No. 13/117,227 filed on May 27, 2011.
Which is Division filed case (#R-6) (#R-5) (#R-4) (#R-3) (#R-2) (#R-1) as below list.
U.S. application Ser. No. 16/298,110 (hereafter as #R-6) filed on Mar. 11, 2019, now is Pending. Which is Division of
U.S. application Ser. No. 16/285,631 (hereafter as #R-5) filed on Feb. 26, 2019, now is Pending. Which is Division of
U.S. application Ser. No. 12/242,762 (hereafter as #R-4) filed on Nov. 27, 2018, now is Pending. Which is Division of
U.S. application Ser. No. 14/739,666 (hereafter as #R-3) filed on Jun. 15, 2015, now is allowed. Which is Division of
U.S. application Ser. No. 14/739,499 (hereafter as #R-2) filed on Jun. 15, 2015, now is allowed. Which is Division of
U.S. application Ser. No. 14/739,397 (hereafter as #R-1) filed on Jun. 15, 2015, now is U.S. Pat. No. 10,184,624 issued on Jan. 22, 2019 which is Division of
U.S. application Ser. No. 11/806,285 (hereafter as #R-2007) filed on Dec. 15, 2007
Which is Division of
U.S. application Ser. No. 11/806,284 (hereafter as #Q-2007) filed on Dec. 15, 2007 now is U.S. Pat. No. 7,630,004

BACKGROUND OF THE INVENTION

For the LED night light with multiple function,
The current invention is
Division file case of
(#VVV-1) U.S. application Ser. No. 14/817,675 filed on Aug. 4, 2015 now allowed,
Which is Division of
(#VVV-2013) U. U.S. application Ser. No. 13/910,295 filed on Jun. 5, 2013 now is U.S. Pat. No. 9,732,921,
Which is Continue of
(#FFF 1D) U. S. application Ser. No. 16/686,525 filed on Nov. 18, 2019,
Which is Division of
(#FFF-2011) U.S. application Ser. No. 13/117,227 filed on May 27, 2011.
Which is Division filed case (#R-6) (#R-5) (#R-4) (#R-3) (#R-2) (#R-1) as below list.
U.S. application Ser. No. 16/298,110 (hereafter as #R-6) filed on Mar. 11, 2019, now is Pending. Which is Division of
U.S. application Ser. No. 16/285,631 (hereafter as #R-5) filed on Feb. 26, 2019, now is Pending. Which is Division of
U.S. application Ser. No. 12/242,762 (hereafter as #R-4) filed on Nov. 27, 2018, now is Pending. Which is Division of
U.S. application Ser. No. 14/739,666 (hereafter as #R-3) filed on Jun. 15, 2015, now is allowed. Which is Division of
U.S. application Ser. No. 14/739,499 (hereafter as #R-2) filed on Jun. 15, 2015, now is allowed. Which is Division of
U.S. application Ser. No. 14/739,397 (hereafter as #R-1) filed on Jun. 15, 2015, now is U.S. Pat. No. 10,184,624 issued on Jan. 22, 2019 which is Division of
U.S. application Ser. No. 11/806,285 (hereafter as #R-2007) filed on Dec. 15, 2007
Which is Division of
U.S. application Ser. No. 11/806,284 (hereafter as #Q-2007) filed on Dec. 15, 2007 now is U.S. Pat. No. 7,630,004
For the Multiple function wall cover light,
This is continuous filing case of co-inventor's U.S. Ser. No. 13/910,295 filed on Jun. 5, 2013, Multiple Function wall cover plate has built-in USB and light means.
This is continuous Filing case of the co-inventor's U.S. Pat. No. 7,318,653 which has built-in Outlets and LED(s) light on the wall plate cover.
The current invention for USB Charger related products has built-in liquid and display unit which is same as co-inventor prior art U.S. Pat. Nos. 5,926,440 and 7,909,477 for the liquid with medium and decorative piece(s) and miniature-piece(s) fill within the container for different Light source means.
The current invention is continuously filing for co-pending filing Ser. No. 13/870,253 (#TTT) wire arrangement for hand-reachable desktop USB Charger related products file on Apr. 22, 2013, now is U.S. Pat. No. 9,559,472 issued on Jan. 21, 2017.
The current invention is continuously filing for co-pending filing Ser. No. 13/863,073 (#SSS) The Power station or products has built-in USB & LED unit(s) for Desk Top installation filed on Apr. 15, 2013.
The current invention is continuously filing for Co-pending filing Ser. No. 13/858,046 (#RRR) wire arrangement for USB Charger device which has the add-on or built-in wire arrange-means for USB charger filed on Apr. 8, 2013.
The current invention is continuously filing for co-pending Filing Ser. No. 13/161,643 (#GGG-II) filed on May 27, 2011, Desk Top LED device has USB unit to charge other electric or digital data device(s).
The current invention is continuously filing for co-pending filing Ser. No. 13/117,227 (#FFF) filed on May 27, 2011, Universal module for USB unit or/and outlet-unit for electric or digital data device(s).
The current invention is continuously filing for co-pending filing Ser. No. 12/950,017 (#CCC) multiple surface LED light has USB/Outlets/LED.
The co-pending invention disclosure the desktop hand-reachable USB-charger related products has wire-arrangement so the wires for receiving-means including USB-ports, outlets receiving socket, LED-units or its any combinations has wire arrangement to offer people hand-reachable charger or power on desk surface including top or other surface and each application has built-in wire arrangement for optional for more convenience to people.

The co-pending invention main features including:
1. The USB and LED(s) light install within the multiple cover plate which will make the device thinner compact size than plug-in type overlay the existing wall cover plate.
2. Built-in wire arrangement to coil, wrap, roll, storage, release AC power wire or other wires related to the said USB Charger operation needed. No more mess AC wire or other wires for charging kits as co-pending filing Ser. No. 13/858, 046. (#RRR)
3. The basic model has built-in USB and LED(s) light selected from all kind of market available LED(s) not only can charge the other electric or the digital data device but also offer at least one of area and charging status and surge indicator and or other preferred type for illumination. Here preferred for LED(s) light with co-inventor's a lot of prior arts including more than one LED, More than one optics element(s), more than one functions, more than one reflective and-or refractive and others; to make the LED night or cover light has the best light performance.
4. Optional can make flat and big size night light or cover light to add top of the said existing the wall cover and has built-in plurality of outlets to offer people more outlets receiving means to connect more external electric or digital data devices.
5. USB Charger output-end power min. has 1.0 Amp up to N-Amp which is not able get from laptop USB ports or other portable or travel USB chargers. The co-pending desk top items with USB ports that apply the Up-grade USB port can supply more wattage output from 12 Watt to much higher wattage from up-grade USB which is announced on 2010. To Apply the up-grade USB port, To full charge be-charged battery no need long time to wait, so save people time to wait fully charged all electric or digital data device(s).

The current invention back to the date Apple i-phone 1 announced on 2007 and till the 2011 i-phone start to use the USB ports and stop to use the original multiple-pin connector for charging and data delivery.

However, for "LED night light has built-in Outlet(s)" as current claim 13 and below text, the current inventor filed this concept on 2007 and all its child filed case(s) as above list and discussed, It is appreciated all the above list and co-pending case all text, concept, idea, construction should all fall within the current invention and all scope of claims.
6. The wire arrangement by roller, retractable set, spring unit(s), twister set(s) which allow people keep all charging related wires, AC power wire storage well and not make a mess for house.

This is the continuously filing case of the co-inventor's Ser. No. 10/954,189, filed Oct. 1, 2004 now abandoned for Electro-Luminescent wall cover plate.

From Parent filed case (#VVV-2011) and (#VVV-1) both shown, The current invention one of preferred products. Both disclosure a movable-piece to make the wall cover can fit for all kind of different style of the wall inner receptacle kits which majority has 2 type (A) 2 oval-shape receptacles with center screw hole (B) 1 rectangular-shape receptacle without central screw hole but has top and lower screw holes so to add the movable-piece can fit for (A) type receptacle, while move-out the movable-piece can fit for (B) type receptacle. The said current invention's wall cover will become a universal wall cover to fit all market major different wall inner receptacle. However, the current invention also including the said non-universal wall cover for (A) or (B) type only. It is appreciated any Wall Cover has built-in USB Charger will fall within the current invention claims, scope.

The other features including above discussed including wire arrangement by add-on elastic unit(s) or built-in groove, frame, hook, ditch, bar, holder, frame, extendable or retractable piece(s); to fit the charging wires which for USB Charger, electric device, i-phone, i-pad, digital device, consumer electric device, communication device, computer device as long as the wire has one end has the USB-plug to insert into the said USB Charger's receiving ports all belong to the wire which can make wire arrangement for current invention wall cover.

The current invention mainly for update Night light or cover light has built-in LED(s) light source and the said receiving port(s) or end(s) including any combination of the said USB charger, AC power source, optional other electric devices as the co-inventor's prior arts for multiple function LED night light or LED cover light.

A multiple function night light or LED or wall cover light has been disclosed in several prior patents, including U.S. Pat. Nos. 6,714,725, 6,810,204, 6,832,794, and 6,839,506, but the prior multiple function wall cover plates have a relatively thick housing and are very dangerously to children because the chemical refill can easily be removed. The current invention uses a screw to security lock all components and prevent children from touching chemical containing components. In addition, whereas the thicker body of the prior multiple function wall cover plates are too ugly because the multiple function components are added-on the existing wall cover plate (not replace it), the current invention's concept is to replace the existing wall cover plate so that the thickness will be much less than that of the prior art. In particular, the current invention uses a conventional commercially available refill component which has the dimension 6.5 cm (Length)×3.5 cm (Width)×0.8 cm (High) and simply installs it on the back housing to reduce thickness and improve appearance.

The co-inventor's prior art as above listed for LED night light or LED wall cover light incorporates (1) an air freshener, and (2) a nightlight, which may include an electroluminescent (E.L.) element, LED, incandescent light, fiber optics, a fluorescent light, or a black tube, and related circuitry for the light source, and (3) a receptacle arrangement (which may include any number of receptacles) to let the LED night light or LED wall cover light offer the best functions to consumers. But lack of the USB Charger which is the main function for update application which is not available on the co-inventor's prior art filing date (i-phone 1 came out on 2007 apply multiple pins connector, and USB port start to apply to i-phone from 2011). The current invention also has the super compact of USB Charger circuit in a (Aa) USB-unit or (Ab) USB-module or (Ac) sealed-unit or (Ad) universal module as the co-pending filing as above discussed Ser. Nos. 12/161,643, 12/117,227, 12/950,017 for these (4) parts definitions and co-pending (#GGG-3-C) Desk top items has USB unit or USB module to charge other electric device and digital device filed on Jan. 26, 2015 and U.S. Ser. No. (#GGG-2011) has more details drawing on Page A, Page B, Page C, Page D for these parts definition and actually photos as illustration. The (#GGG-family) mainly for the desk top USB charger system. Not for Wall Plug-in products.

The co-inventor disclosure current invention for update technical and offer people for more convenience to charge the electric device or digital data device from built-in LED night light or LED wall cover is big improvement than other USB Charger is not permanent install on the wall. The USB charger need special circuit which need change the input AC current into DC current which is not needed for co-inventor's U.S. Pat. No. 7,318,653 so this is brand new and different concept, technical, skill, construction with U.S. Pat. No. 7,218,653 as below more detail discussion.

Other prior art includes U.S. Pat. Nos. 6,716,256; 6,657,380; 6,642,452; 6,413,598; 6,388,345; 6,342,995; 6,089,893; 6,086,211; 6,050,716; 5,934,451; 5,899,549; 5,842,763; 5,683,166; 5,670,776; 5,660,459; 5,637,930; 5,586,879; 5,544,025; 5,485,356; 5,407,721; 5,117,734; 4,924,349; 4,774,641; 4,755,913; 4,739,187; 4,617,613; 4,546,419; 4,514,789; 4,255,780; 4,240,090; 4,038,582; and 3,895,225, as well as the Inventor's prior U.S. Pat. Nos. 6,280,053; 6,171,117; 6,170,958; and 6,183,101. None of these prior art patents discloses a multiple function LED night light or LED wall cover plate light because these prior art(s) is out-of-date products which applied the high-heat and super big size incandescent bulb(s) such as C7 5 Watt bulb inside. Those is no need AC-to-DC circuit. The current invention having a plurality of functions including (1) fragrance(s), (2) receptacle(s), and (3) nightlight(s) to easily replace the original wall outlet's cover plate and provide electricity delivery from the prong(s) of the multiple functions wall cover plate as in the current invention described below, and in particular, a multiple function wall cover plate having the shape and thickness of an existing wall outlet and a safety screw to prevent children from touching any parts of a refill, the nightlight, or the receptacle.

The co-inventor's prior art for multiple function LED cover light mainly teach a multiple function wall cover light which has (1) Outlets (2) Light device and other functions including description as below:

(1) From FIGS. 22 and 23 shown—Air Fragrance

FIG. N shown at least one ventilation slot (s) to allow the inside refill's fragrance (103) to be spread out to the environment, and (2) From FIGS. 22 and 23 shown—LED(s) Light Source One of preferred LED night light or cover light as FIG. N shown at least one nightlight emit out area(s) or opening(s) or lens(es) or window(s) or hole(s) of LED night light or LED wall cover light that incorporates at least one of LED(s) light source or may be selected from the group consisting of an electro-luminescent (EL) element, LED, incandescent light, neon light, fluorescent tube, black tube, gas filled light source, or any equivalent light source to offer a nightlight function.

(3) From FIGS. 22, 23 shown—FIG. M shown one of preferred LED night light or cover light has built-in Number of Outlets Receptacle FIG. M shown the multiple function LED Night light or LED wall cover plate light includes at least one pair of receptacles to keep the existing wall outlet functions without reducing the number of receptacles while adding multiple functions LED night light or LED wall cover light top of the existing wall cover plate.

(4) From FIGS. 22, 23 shown—Openings for Scent or Light Emit Out

FIGS. M and N show details of the preferred housing with number of openings, grills, windows, cutouts, hole(s) to allow the scent or smell of the refill to spread out quickly. These openings, grills, windows, or cutouts also can allow the inner at least one LED(s) to emit at least one of LED light beam out which is at least one of area(s), or charging status, or surge/other protection system status, or position indicator illumination.

(5) From FIGS. 22,23 shown—Center Screw to Fasten Wall Cover to Inner Kits

The multiple function LED night light or LED wall cover plate light, while the product is one of LED wall cover plate light, it has a center screw hole to allow the multiple function wall cover plate to be securely fastened by a screw though the original outlet's screw hole and replace the original outlet's wall cover plate.

(6) From FIGS. 22 and 23 shown—Prong to Get the Power from Wall Outlets

The multiple function LED night light or wall cover plate also has at least one pair of prong sets which can be easily inserted into the original wall outlet's receptacle and supply electricity from the original wall outlet to the multiple function wall cover plate's receptacle or receptacle(s)

The current invention has following features as below details:

<1> the Current Invention has USB Charger Unit

The said USB charger unit has input AC current and circuit to change from AC input current to the DC current which is not existing for co-inventor's earlier prior art. The AC-to-DC transformer, invertor also not existing on earlier co-inventor's earlier prior arts. The co-inventor's prior art to offer the AC-outlets to let people had the more outlets while use replaced wall cover which has 2 outlets, but current invention for multiple wall cover has at least 2, 3, 4, 6 outlets. So, the earlier filed case only increased 1, 2, 3 outlets to get the AC power. The current invention not only have more outlet(s) but also has 1 to N (N is any number) of USB related charger to charge all device(s) has the energy storage kits inside such as rechargeable batteries, capacitors . . . so the current invention is not same as earlier night light or cover plate light in concept, construction, application, electric components and size, shape which only need several conductive-metal piece can make the AC current receiving outlet(s) to receive other AC operated product(s) male AC plugs inserted into to make electric delivery. So big difference with the inventor prior art has only conductive metal piece v.s. current invention for USB charger need a lot of electric components including preferred combination selected from transformer, invertor, capacitor, resistor and control system . . . etc, to change the AC input current through prong to DC current.

<2> the Current Invention has Light Arrangement Shown on at Least One of the Front Surface, Housing, Front Lens(es), Opening(s), Window(s); for Illumination or Charging Status Indicator Light or Surge/Other Protection System Status Light.

This is not same as co-inventor's prior art the light is emit out from housing side surface as inventor's prior arts. The inventor's light performance from side walls of unit with opening, hole, grill which is not able to work as emergency light, power fail light, motion sensor light, remote control light to offer illumination to people for front area(s).

The current invention light arrangement is on all preferred area(s), window(s), opening(s) with or without integrated circuit (IC) as drawing shown FIG. 10 to FIG. 21.

<3> the Current Invention the LED Light Source for Illumination No Need Extra AC-to-DC Circuit Because USB Charger Already had AC-to-DC Circuit.

The current invention has built-in USB charger already had the DC power source so can directly offer the power to said number 1 to N LEDs, so the current invention no need individual AC-to-DC circuit to get DC power to said Number 1 to N LEDs like the inventor's prior art because lack of the USB Charger so need has individual circuit to get DC power source for said LEDs. This is also major different for the current invention with inventor's earlier prior arts.

<4> the Current Invention is Overlay or Top of Existing Wall Cover

The current invention to (a) install or (b) fasten (For anti-theft) the screw with inner kits which is not limited for one center screw, some preferred inner kits need to fasten the top & lower screw holes not the center screw. The market had different inner receptacles one for center screw fasten, One for (top and low) 2 screw to fasten, so inventor's prior art is not same as current invention for LED night light or cover light install on top of the said existing wall cover plate by prong not only to fit on location but also get power source.

<5> the Current Invention is a Universal LED Night Light or Cover Light

One of preferred embodiment which is wall cover light has opening to exposed one of wall outlet(s), the preferred embodiment as FIG. 1 to FIG. 9 has movable-piece so can fit for all kind of different inner kits (inner receptacle for 2 oval-shape or 1 rectangular-shape outlets) so can have one LED wall cover light to fit all kind of market available inner kits. This is not workable for the inventor's prior art only by center screw. This is big improvement for consumer never buy wrong wall cover.

<6> the Current Invention LED Wall Cover Light is Universal for all Market Inner Receptacle Shape The current invention has details contour shaped arrangement and movable-piece details construction so can fit for all kind of the said all kind of the 2 oval-shaped or 1 rectangular-shape inner kits. This is not available for inventor's prior art for such so detail match for all kind of inner kits' shape.

Also, the current invention different with other US Prior arts including:

1. US Prior art; US 2012-027-6763 Quezada, Anthony, This prior arts is for inner receptacle unit, Not for a LED plug-in wall cover light, so '763 is totally different with current invention for any aspects including concept, design, application, electric, assembly.

2. US Prior Art; U.S. Pat. No. 3,297,886 DANNER EUGENE G, The '886 filed on 1967 old time invention which only for the outlets which is get AC input power from wired plug and get AC output power for 2 prongs external electric device to supply AC power source. This is nothing to do with the current inventions for USB charger at all. This 1967 invention belong to classification for power tap or adaptor, not belong to USB charger. Also, The USB invention is not on the 1967.

3. US Prior art; U.S. Pat. No. 6,540,554 McCarthy, David G., The '554 teach a desk top power station which is not belong to plug-in wall outlet application. Also, the 2001 filed the case the inventor only show the (1) AC outlets (2) Communication receiving pots as items (12) for telephone, or telex, or fax equipment line to insert into for the parts (12) so this is no any relation for USB charger, furthermore, the USB connect-wire with (i) Type A and Micro USB or (ii) Type A and Type C to connect with be-charged phone or pad is not existing. I-phone from Apple company on 2007 and i-phone has USB ports not use plurality number pins start from 2011, so on 2001 still not come out USB ports for charge phone or other be-charged communication device(s), so '554 is out of date and belong to old date application.

4. US Prior art; US 2009-031-5509 Wu, Johnson, The '509 has built-in power source As claim line 8 and 9 clear the power source inside the socket (10). This invention is not for plug-in Wall cover with inner receptacle to build the power source. Also, the socket (10) has internal power source which is not same as current invention get AC power source by prongs insert into wall inner receptacle receiving means. So this is no any same concept, construction, design, application.

5. US prior art; U.S. Pat. No. 7,318,653 Chien, Tseng-Lu is current inventor earlier filed case, and all the difference between the inventor's prior art v.s. current invention scope, drawing, concept, construction, design, features as above discussed from Point (1) to (6) and <1> to <6> has big improvement including:

(i) Let people can has simple replacement existing non-USB charger wall cover become a permanently install wall cover, and current invention product(s) has Not only USB charger, keep outlet, and has light for illumination so current invention has more than 2 functions added top of USB Charger and Illumination. And (ii) This is most cheap and non-expensive for all hotel, house, office, to make the modern remodel to has the USB charger on wall outlets without need to spend big money for built-in USB charger and light for tiny wall outlet space and not able to let people to steal while use the anti-theft screws for permanently tighten with inner receptacle kits.

(iii) The current invention has universal moveable unit or piece so can fit all the different inner receptacle shape and configuration. None of market model has this for wall cover USB Charger.

(iv) DD. The current invention build the electric delivery from home electricity to USB charger no need to touch live wire so it is simple and even kids can make replacement for this plug-in wall cover.

(v) The current invention built-in the added function including listed functions which will bring people more convenience including optional (1) outlets device, (2) electric devices(s), (3) LED light device, (4) EL light device, (5) Florescent tube device, (6) power fail light device, (7) illumination device, (8) Wi-fi device, (9) internet device, (10) wireless router device, (11) time piece, (12) motion sensor device, (13) Remote control device, (14) Blue tooth device, (15) wi-fi and/or wi-fi extender system, (16) internet system, (17) Video Camera device, (18) Recording device, (19) Memories unit(s), (20) digital data storage unit(s), (21) Power unit(s), (22) Energy saving device(s), (22) Energy storage device, (23) Batteries, (24) DC Power source(s), (25) conductive pieces, (26) prong, (27) electric parts and accessories. (28) Optics piece(s), (29) reflective piece(s), (30) optics lens(s), (31) light traveling medium or piece(s); to make the said LED night light or LED Wall cover light has built-in more than one function which at least has one of USB means.

Hereafter has following drawing, brief description and details description as below:

BRIEF DESCRIPTION OF THE DRAWINGS

FIG. 1 FIGS. 1-2 and FIGS. 1A, 1B, 1C shown one of preferred embodiment for multiple function LED night light or LED wall cover light has number of USB charger and built-in light source to offer illumination or show charging status which has moveable piece to make the one products can fit for all kind of the inner receptacle shape and construction under the wall cover plate.

FIG. 2 and FIG. 2A, FIG. 2B, FIG. 2C is one of preferred LED night light or LED wall cover light has 2 USB receiving ports and has details construction for back side and show the relation of the back base, movable-piece so can fit for traditional (2 separated oval-like receptacles) or decorative (1 pc rectangular-shape receptacle) inner AC outlets receptacle under the existing wall cover plate.

FIG. 3A is 2 separated oval-like receptacle and (2) FIG. 3A is a one piece rectangular-shape receptacle with the said 1 port (FIG. 3) USB Charger or 2 port (FIG. 4) USB charger preferred embodiment of the current invention of the multiple functions wall cover plate.

FIGS. 10,11,12,13,14,15,16,17, 18, 19, 20, 21, 22, 23 show preferred embodiments which has desire any combination or different assortment for USB and LED(s) and other parts for LED night light or LED wall cover light. The parts and accessories for preferred assortment selection from the (1) optional outlets device, (2) electric devices(s), (3) LED light device, (4) EL light device, (5) Florescent tube device, (6) power fail light device, (7) illumination device, (8) Wife device, (9) internet device, (10) wireless router device, (11) time piece, (12) motion sensor device, (13) Remote control device, (14) Blue tooth device, (15) Video Camera device, (16) Recording device, (17) Memories means, (18) digital data storage means, (19) Power means, (20) Energy saving means, (21) Energy storage device, (22) Batteries, (23) DC Power means, (24) conductive means, (25) prong means, (26) electric parts and accessories means. (27) Optics means, (28) reflective means, (29) optics light traveling means to make the said Wall cover has built-in more than two functions which at least has USB means and Light means.

Figure 22:
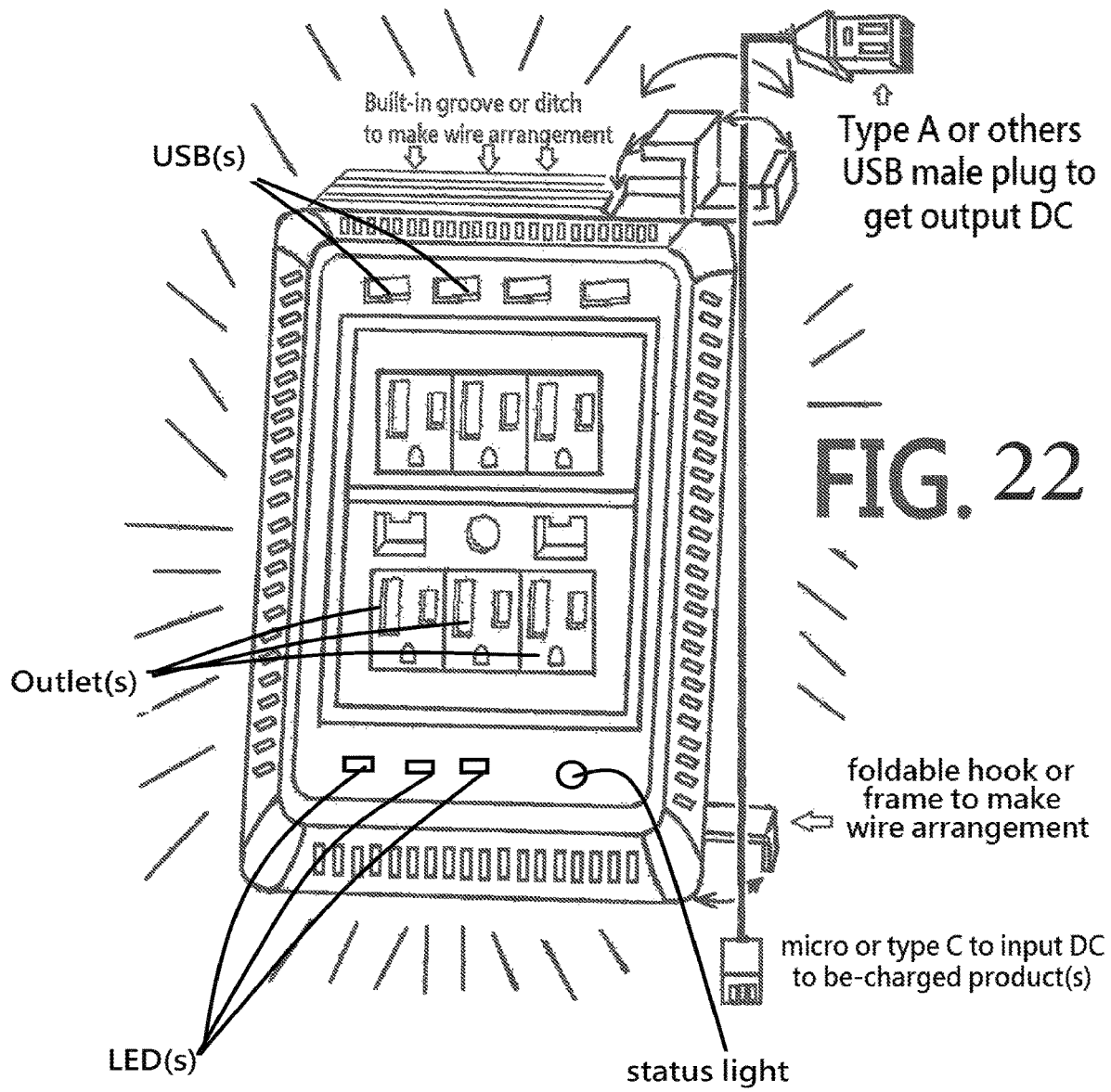

Also, FIG. 22 disclosure the wire arrangements for LED night light or LED wall cover light as above discussed which inventor has co-pending filing U.S. Ser. No. 13/858,046 (hereafter as #RRR), U.S. Ser. No. 13/863,073 (hereafter as #SSS), U.S. Ser. No. 13/870,253 (hereafter as #TTT) for details wire arrangement for the USB Charger. From FIG. 22 can see the built-in groove, ditch, frame, bar, pole, extendable and retractable, foldable arms; to make wire can wrap around the housing or has the foldable frame, hooks to make the wire to coil with opening to tight or fix wire on certain coils. The other said wire which means the electric conductive wire has the one end is USB-plug which allow plug into USB-receiving ports to build the electric delivery from USB Charger to the said other electric device or digital data device which may including for communication, consumer electric, computer device's wire all fall within the said wire arrangement's wire definition.

Figure 23:
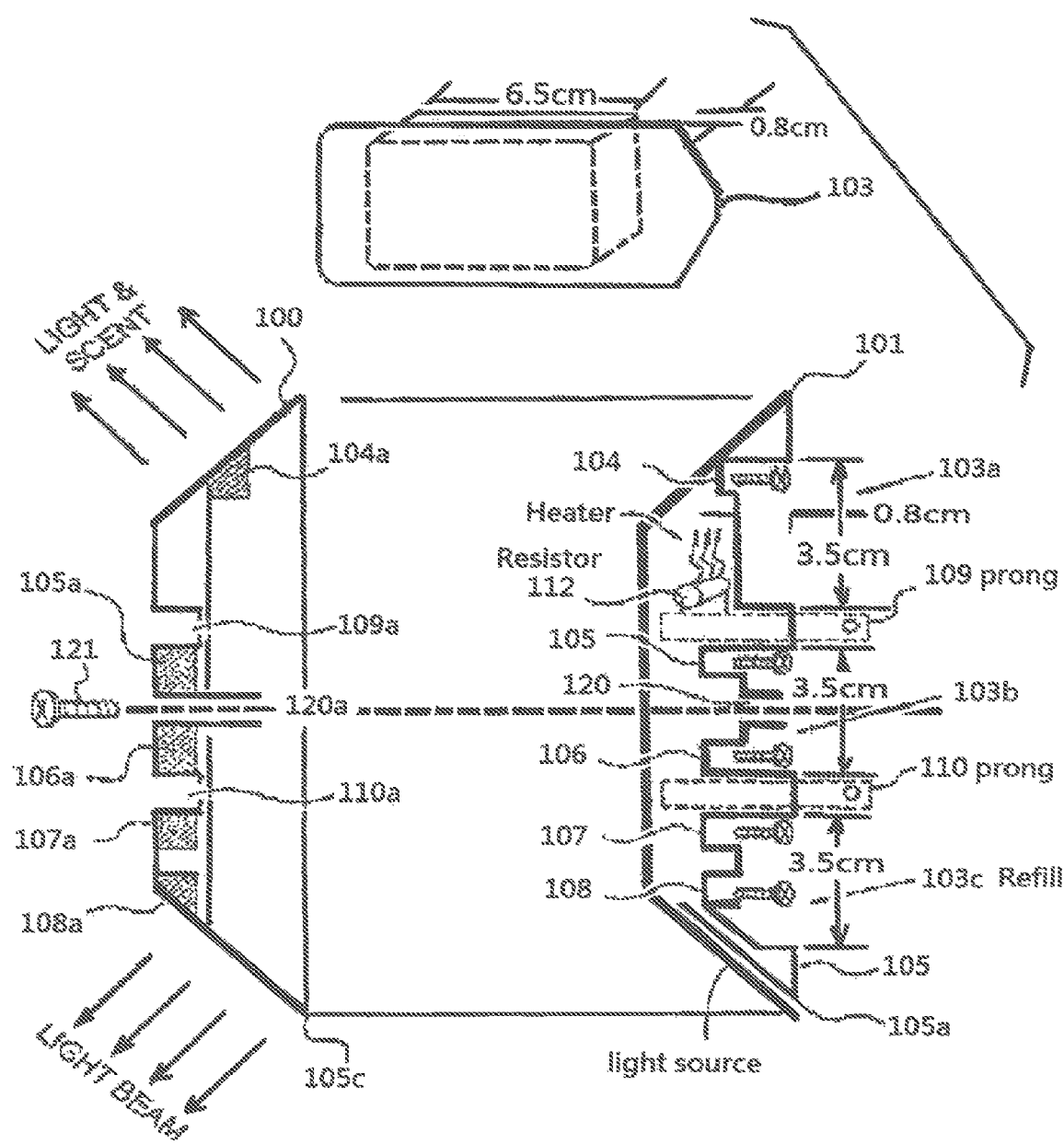

FIG. 23 is co-inventor's prior art LED night light or LED wall cover light which a side-view of showing the front cover and back base of earlier embodiment which has (1) AC outlet receiving means (2) Light source (3) Air Freshener with center screw to fasten and connect with wall AC power source by prong means.

DETAILED DESCRIPTION OF THE PREFERRED EMBODIMENTS

FIG. 10,11,12,13,14,15,16,17, 18, 19, 20, 21, 22, 23 are preferred LED night light or LED wall cover light embodiments which has desire any combination or different assortment for USB and Light wall cover may has optional selection from the optional (1) outlets device, (2) electric devices(s), (3) LED light device, (4) EL light device, (5) Florescent tube device, (6) power fail light device, (7) illumination device, (8) Wife device, internet device, (9) wireless router device, (10) time piece, (11) motion sensor device, (12) Remote control device, (13) Blue tooth device, (14) Video Camera device, (15) Recording device, (16) Memories means, (17) digital data storage means, (18) Power means, (19) Energy saving means, (20) Energy storage device, (21) Batteries, (22) DC Power means, (23) conductive means, (24) prong means, (25) electric parts and accessories means. (26) Optics means, (27) reflective means, (28) optics light traveling means to make the said Wall cover has built-in more than two functions which at least has USB means and Light means.

From FIG. 10,11,12,13,14,15,16,17, 18, 19, 20, 21, 22, 23 shown all different function LED night light or LED wall cover light has built-in USB and light means with additional other electric functions Each different Wall Cover has different multiple-Functions with clear functions are shown on each drawing. The said From FIG. 10,11,12,13,14,15,16,17, 18, 19, 20, 21, 22, 23 disclosure the difference for the LED night light or LED wall cover light for multiple functions with built-in USB and light device with optional to add more functions. These embodiments have the (1) central hole or (2) top & lower holes and to use screw or screw(s) to fasten the said Multiple functions LED night light or LED wall cover light on the existing wall cover's inner kit's screw hole(s) to fix the position. The said multiple function(s) LED night light or LED wall cover light which can replace the existing non-functional wall cover plate or overlay top of the existing wall cover because the electric delivery from the inner kits to the multiple function(s) LED night light or LED wall cover light are made by conductive piece here of preferred is a prong set(s) which has or has not the ground pole.

The electric delivery from wall inner kits though the said prong or prong(s) to the Multiple functions LED night light or LED wall cover light circuit to supply the AC electric signal to the multiple function LED night light or LED wall cover light circuit board to make the said multiple functions related circuit board work under pre-determined functions including (A) to change the AC electric signal to DC electric signal to charge the any DC energy storage device such as i-phone, i-pad, smart phone, communication device, consumer electric device or (B) the outlet receiving means to supply the AC electric signal to the AC powered device such as Laptop computer or computer related parts or equipment such as printer, scanner, fax machine or the like.

From FIG. M shown the multiple functions LED night light or LED wall cover light has bigger size than existing wall cover so it can cover whole area of existing wall cover and its respectively hole on the surface to align with the inner receptacle's hole position to use (1) central screw or (2) 2 side screws to fasten the said multiple function wall cover plate with the wall inner receptacle holes.

The current invention of multiple functions LED night light or LED wall cover light as long as not smaller than the existing wall cover plate. It is appreciated that any size bigger than the existing wall cover plate should be still fall within the current invention scope. The current invention also disclosure the multiple functions LED night light or LED wall cover light is top or overlay the wall inner AC receptacle's outlets receiving unit(s) at least one piece or overlay the all wall inner AC receptacle's outlets receiving means all pieces(es) depend on market requirement.

From FIG. 10,11,12,13,14,15,16,17, 18, 19, 20, 21, 22, 23 also may incorporate with wire arrangement for the preferred embodiment as long as there existing a space with some wire hold-means (Not shown), The wire can be well arrangement within the space to prevent from a mess wire as the co-pending filing case Ser. Nos. 13/870,253, 12/858,046 drawing and details description so not discuss here. It is appreciated all the above list co-inventor's prior art, co-pending filing all content and drawing and description all refer to this new filing still be consider as scope of the current invention and not limited for the words, details listed on this filing case.

From FIG. 10,11,12,13,14,15,16,17, 18, 19, 20, 21, 22, 23 shown the current invention has following 12 features as below:

1. A multiple function LED night light or LED wall cover light arranged to install on wall outlets inner kit's receiving unit(s), comprising:

at least one front cover and a back base assembled to the front cover to form said multiple function wall cover plate, said multiple function LED night light or LED wall cover light having a shape corresponding to that of the existing wall plate, wherein the multiple function LED night light or LED wall cover light is fastened by means of at least one of screw extending through the front cover, and/or back base, and/or movable piece to a wall existing inner receptacle's plate holder;

at least one prongs arranged to supply electricity from an wall existing receptacle and the said prongs covered by the multiple function LED night light or LED wall cover light while the prongs insert into said at least one wall inner receptacle, \ said USB charger or optional said light kits installed within the front cover and back base and has its circuit, USB charger's receiving port(s), and related electric-parts or accessories. And at least one pair or prong or false prong extending rearwardly from back base for insertion into said wall existing outlet's inner receptacle, said USB charger's receiving port(s) or optional variety type or shape or construction of receiving kit(s) for inserting USB plug, prong, Adaptor, or contact unit(s) of said external electric or digital data device(s);

at least one light source installed within between said front cover and back base to emit light through said front cover or contour or body or parts of the said multiple function LED night light or LED wall cover light and thereby provide a lighting effects under predetermined function, performance including offer illumination, indicator for charging status.

The said multiple function LED night light or LED wall cover light get power from wall outlet's inner receptacle whenever the said built-in prong is connected to the existing wall inner receptacle and also power the said controller of the said USB Charger's and said light device's circuit, sensor, switch, CDS, Motion Sensor, Power fail sensor, blue tooth sensor, IC, Or any other electric or electronic control device(s);

The said USB charger of the said multiple function LED night light or LED wall cover light which get outlet power as AC input power and passing though the transformer, invertor, or adaptor and related electric parts & accessories to make the input AC current to desired DC current to charge the said external electric device(s).

The Said USB charger has at least one USB receiving ports.

2. A multiple function LED night light or LED wall cover light, further comprising at least one LED or Electroluminescent, florescent tube means, or other light means connected with the IC or sensor means or switch means, blue tooth means, remote control means for desire light effects with pre-determined function performance, effects.

3. A multiple function LED night light or LED wall cover light, wherein said wire arrangement means is permanently designed on said wall cover plate or add-on design to make the said any wire can be well arranged and storage.

4. A multiple function LED night light or LED wall cover light, wherein a number of said at least one or all the wall inner receptacles of the existing wall outlet inner kits are overlayed by the said multiple function Wall cover plate.

5. A multiple function LED night light or LED wall cover light, wherein The said USB Charger may has different output-current from 0.5 Amp, 1.0 Amp, 2.1 Amp, 2.4 Amp, 3.1 Amp, 3.4 Amp, 4.2 Amp, 4.4 Amp, or other current requirement to charge one or more than one the said communication, computer, consumer electric or digital data device at same time.

6. A multiple function LED night light or LED wall cover light, wherein said the other electric parts and accessories has at least one of copper piece(s) is arranged to supply electricity to multiple functions LED night light or LED wall cover light circuitry has respectively controlling means for different functions and also supply the electricity to the said light means, as well as to said at least one of the said optional add other electric functions.

7. A multiple function LED night light or LED wall cover light, wherein The said Multiple function wall cover plate has one movable unit(s) which can add on to the housing to fit for existing 2 separated outlets (more oval looks) wall inner receptacle shape or move out to fit the for decorative rectangular one piece (more rectangular and not separated 1 piece) wall inner receptacle shape.

8. A multiple function LED night light or LED wall cover light, wherein The said variety of shape, construction receiving port(s) is a AC outlet which has the Wall outlet AC input current and offer the same current of the said Wall Outlet's AC current as output current to other electric or digital data device and AC outlet or USB Charger's receiving ports has conductive means or copper piece(s) said copper piece(s) is connected to said existing receptacle by prongs and conductive piece(s) selected from the group consisting of wires, metal material, solder, resilient conductive piece(s), and combination of wires, metal material, solder, or resilient conductive piece(s).

9. A multiple function LED night light or LED wall cover light, wherein said multiple function LED night light or LED wall cover light has dimensions of 12-24 cm by 6-18 cm and the said Multiple function wall cover plate has more than two functions which the third functions is one of the optional outlets device, electric devices(s), LED light device, EL light device, Florescent tube device, power fail light device, illumination device, Wife device, internet device, wireless router device, time piece, motion sensor device, Remote control device, Blue tooth device, wifi means, internet means, Video Camera device, Recording device, Memories means, digital data storage means, Power means, Energy saving means, Energy storage device, Batteries, DC Power means, conductive means, prong means, electric parts and accessories means. Optics means, reflective means, optics light traveling means to make the said LED night light or LED wall cover light has built-in more than one function which at least has one of USB means.

10. A multiple functions LED night light or LED wall cover light, comprising:

at least one front cover and a back base assembled to the front cover to form said multiple function LED night light or LED wall cover light, said multiple function LED night light or LED wall cover light having a shape corresponding to that of the existing wall plate, wherein the multiple function LED night light or LED wall cover light is fastened by means of at least one of screw extending through the front cover, and/or back base, and/or movable piece to a wall inner receptacle's plate holder and replace of the existing wall plate;

at least one prong or prong(s) arranged to supply electricity from an existing wall inner receptacle mounted in said wall and the said wall existing wall inner receptacle is covered by the multiple function LED night light or LED wall cover light which has at least one USB receiving port(s), said USB Charger being installed within the front cover and back base and has prong or prong(s) extending rearwardly from the front cover, and/or back base, and/or movable piece for insertion into said existing wall inner receptacle, said front cover including USB charger receiving-means or optional variety of the receiving-means for inserting USB-Plug or other type plug or prongs or connectors, adaptor of an external device(s);

at least one light source installed within between said front cover and back base to emit light through said body, contour, parts of the said multiple functions wall cover plate and thereby provide a desire light effects whenever the prong, prong(s) is connected to the wall inner existing receptacle and control by sensor means, switch means, power fail means, IC means, remote control means, blue tooth means or other electric or electronic parts & accessories; and at least one additional electrical device(s).

11. A multiple function LED night light or LED wall cover light as claimed in claim 10, wherein said additional electrical device is selected from the group consisting of: a. a fragrance dispenser; b. a other function light; c. an insect repeller; d. a time piece; e. a motion sensor; f. an infrared sensor; g. a blue tooth electrical device controller. h. a wi-fi or router or internet device. i. video or audit devices and j. Wire arrangement means 12. A multiple function LED night light or LED wall cover light has USB, comprising:

at least one front cover and a back base assembled to the front cover to form said multiple function LED night light or LED wall cover light, said multiple function LED night light or LED wall cover light has USB having a shape corresponding to that of the existing wall plate, wherein the multiple function LED night light or LED wall cover light is fastened by means of a screw extending through the front cover, and/or back base, and/or movable piece to a wall existing inner receptacle plate holder to replace the existing wall plate at least one copper means arranged to supply electricity from an existing receptacle mounted in said wall plate holder and covered by the multiple function LED night light or LED wall cover light to said at least one USB receiving port(s), said prong being installed in multiple functions LED night light or LED wall cover light for insertion into said existing receptacle, said front cover including USB charger's receiving port(s) for inserting USB-Plug of an external device(s);

at least one LED(s) light source installed within between said front cover and back base to emit light through said body or part of housing of the said multiple functions wall cover plate and thereby provide a desire light effects whenever the prong or prongs is connected to the existing wall inner receptacle and the light control by sensor, switch, power fail controller, IC, remote control, blue tooth wireless controller or infra-red remote controller, motion sensor, other electric or electronic parts & accessories; or/and at least one additional electrical device(s).

The current invention details description as below;

From FIG. 1 the multiple function LED night light or LED wall cover light (100) has USB charger and built-in Light for illumination or show charging status has front cover (10a) and back base (10b) has the central hole (10g) to allow the screw (not shown) to fasten the said LED night light or LED wall cover light (100) on the inner receptacle center hole (10g') while the inner receptacle is a traditional 2 separated oval-shape outlets (30e'). If the inner receptacle is for decorative receptacle (41f or 62f) it has no central hole so need to fasten the wall cover from the top (14h) and lower screw holes (14i). The LED night light or LED wall cover light (100) has the one USB port (10d1) to allow the other electric device prong means to insert into to charge the other electric device. The optics lens (10m) has one light bar (10n) to guide the two ends LED(s) light (10L) or other preferred area(s); to emit into and make the optic lens (10m) has illumination or show the charging status. The current invention has one important feature for the movable-piece (10c) which can allow the current invention can fit for traditional 2 separated oval shape outlets has central holes (30e') decorative receptacle has 2 outlets without central holes (41f).

From the FIG. 1-2 the LED night light or LED wall cover light has 2 USB ports (11d2) to allow people to charge 2 other electric device at the same time. The current invention has all kind number of the said USB ports from 1 to N (N is any number) depend on market requirement. The said LED night light or LED wall cover light has movable piece (11c) has the oval-shape opening (11e) for the oval-like receptacle (31e', 60e') which allow the wall cover can become universal for any kind of inner receptacle available from market place(s).

From FIG. 1A and FIG. 1B and FIG. 1C can see the movable piece (13c) has center hole (13g) and over-shape opening (13e) which can on the LED night light or LED wall cover light of FIG. 1A. FIG. 1A show the LED night light or LED wall cover light back side view which can see LED night light or LED wall cover light has one pair of prong (12j) which allow to insert into the inner receptacle (31e') while the movable piece (13c) install on the LED night light or LED wall cover light, while the movable piece (13c) move out it will fit for the other type of inner receptacle (41f) because the movable piece has oval-shape opening (13e) so only can fit for inner oval-shape receptacle (31e'). while the movable piece (13c) move out from LED night light or LED wall cover light, there will have the rectangular opening (14f) so can fit the inner rectangular receptacle (41f). This is the current invention added very important features for multiple function LED night light or LED wall cover light has the USB charge and LED(s) light, so the current invention wall cover is universal type. However, it do not have movable piece and come out 2 different type of LED night light or LED wall cover light to fit only one type of inner receptacle but still has built-in USB charger and LED(s) light for current invention. It is appreciated the above discussed the Universal LED night light or LED wall cover light or only can fit one of inner receptacle LED night light or LED wall cover light both are still fall within the current invention as long as the LED night light or LED wall cover light has USB charger and LED(s) light.

From FIG. 1A can see the LED night light or LED wall cover light has movable piece (12c) has the center hole (12g) to allow screw to fasten the wall cover on the inner over-shape receptacle (31e'). The LED night light or LED wall cover light also has the top and low screw holes (12h) (12i) these 2 holes mainly to offer the screw holes for the decorative receptacle (41f) which has no central screw holes. However, if people feel more comfortable like to fasten screw on top and lower screw holes while work for the oval-shape inner receptacle (30e') it is also workable. So, the top and lower screw holes (12h) (12i) can use for any kind of inner receptacle (31e', 41f).

From FIG. 1C see LED night light or LED wall cover light has rectangular opening (14f) for rectangular inner receptacle (41f) and the prong (14j) insert into the inner receptacle (41f) receiving kit(s) to build the electric connection to get power. The said LED night light or LED wall cover light which is not allow people to connect with the inner receptacle's wire and just to plug the prong (14j) into the inner receptacle's receiving hole for safety concern and not need people to cut the live wires and touch the high voltage and big current live wire is other features of the current invention.

From the FIGS. 1, 1A, 1B, 1C can see change the movable unit(s) to fit for different inner receptacle this change is made by a movable-piece (13c) is very good feature for multiple functions LED night light or LED wall cover light has built-in USB charger and LED(s) light not only allow people to charge their communication, consumer electric, computer device but also offer the light illumination or show the charging status is the current invention some features to make big improvement than other charger.

From FIG. 2 show the LED night light or LED wall cover light has 2 USB ports to charge the more than one other electric device(s) same as the earlier discussed FIGS. 1, 1-2, 1A, 1B, 1C which is same as earlier discussion the FIGS. 2, 2A, 2B, 2C show the details how to use movable piece (22c) to change the wall cover to fit for oval-shape inner receptacle (30e') to rectangular-shape inner receptacle (41f) and it can reverse to change from can fit (41f) to (30e') while add the movable piece (22c).

Figure 3A:
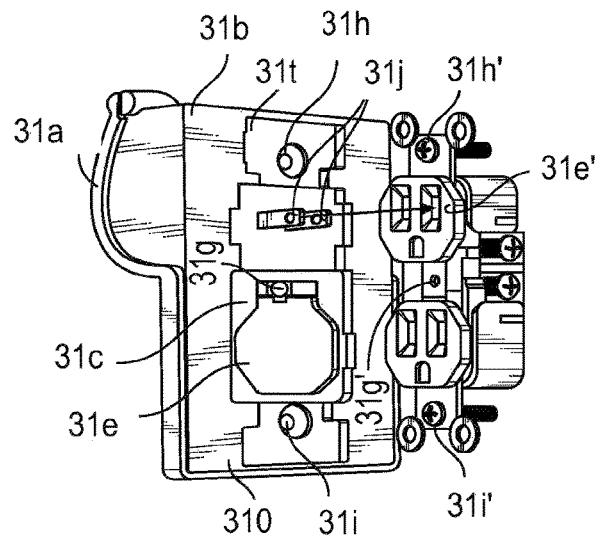
FIGS. 3 & 3A and FIGS. 4 & 4A are current inventor's preferred LED night light or LED wall cover light design which has a side view and back view of the preferred embodiment, Also show the relation for the 2 major outlet receptacle as (1)
Figure 3:
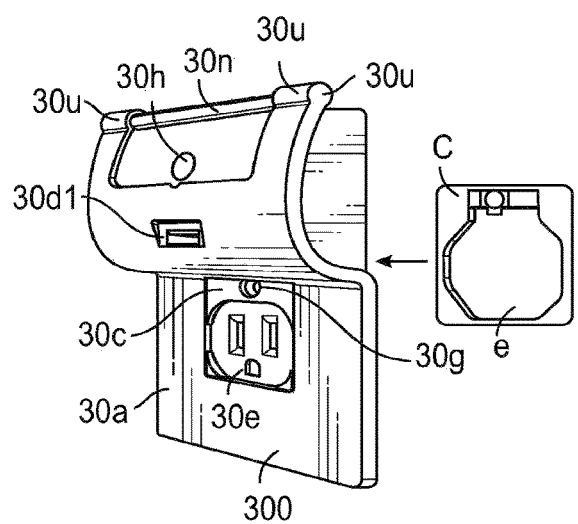

From FIG. 3 to FIG. 3A show the LED night light or LED wall cover light has 1 USB port (30d1) and has center hole (30c) and top hole (30h) and lower hole (30i) while the inner receptacle is over-shape (30e') need the movable piece (30c) on the housing (30a) and the LED night light or LED wall cover light has the top and low half-groove (30u) to hold the optic-lens (30m) light bar (30n) and light bar has two light input end (30v, now shown) to allow light means (30L) emit the light into the light bar (30n) to make the optics-lens (30m) to show the illumination or show the charging status.

From FIG. 3A can see the prong (31j) insert into the over-shape receptacle (31e') receiving holes to get power from wall outlets. The LED night light or LED wall cover light has central hole (31g) to allow screw to fasten with inner receptacle central hole (31g') so can solid tighten the LED night light or LED wall cover light with wall inner receptacle and the LED night light or LED wall cover light opening (31e) allow at least one of the inner receptacle one of outlets show and let the people to use.

Figure 20:
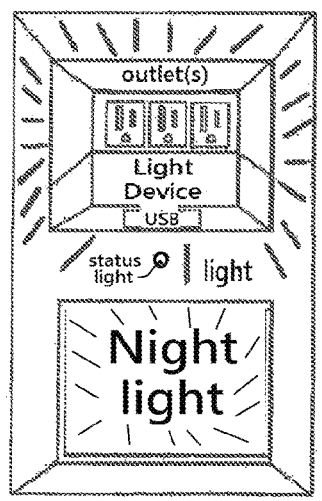
Figure 21:
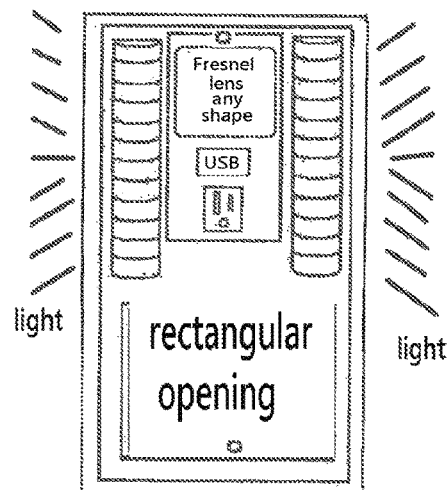

From the FIG. 20,21,22 also show the current invention also can have built-in number of outlets on the LED night light or LED wall cover light, so can make-up the one of the wall outlets been use for current invention to get power for the current invention as power source and inserted by LED night light or LED wall cover light prong (31j).

Figure 4A:
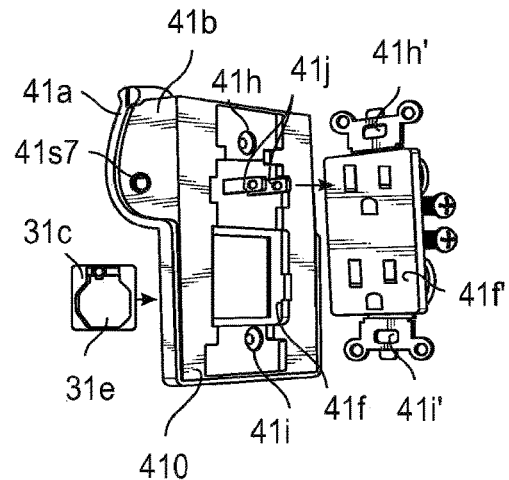
Figure 4:
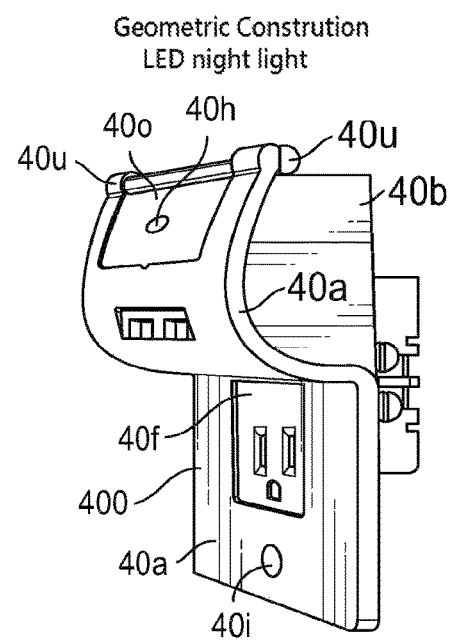

From FIGS. 3A, 4A show the function of the movable piece (c) function to interchange the LED night light or LED wall cover light from oval-shape outlets to rectangular-shape outlets just add or move-away the movable piece (C). Same as FIGS. 3, 4 for the front viewing for same features.

Figure 5:
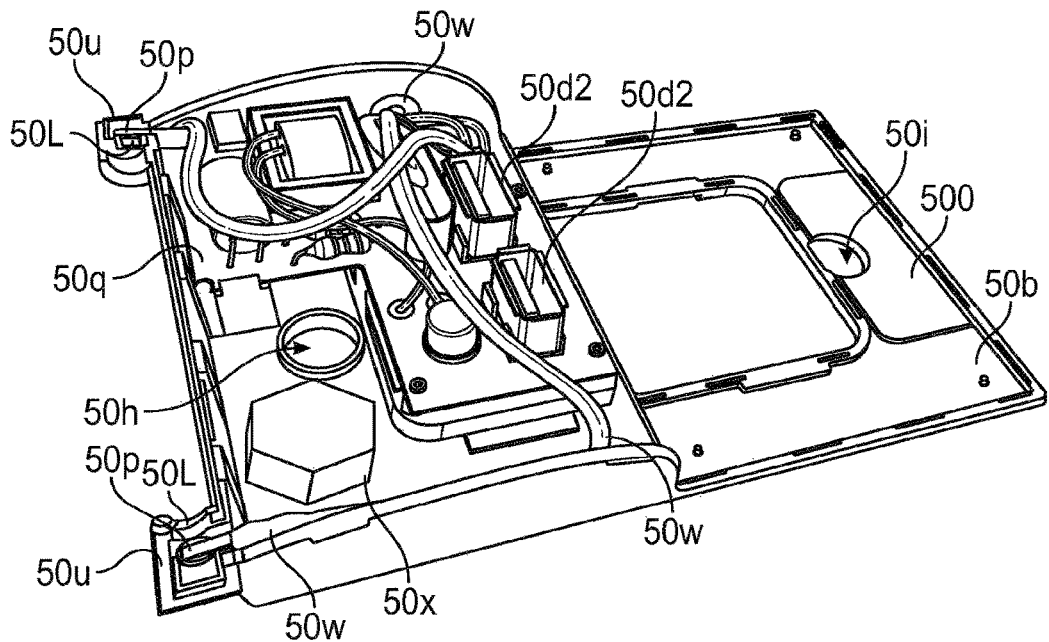
FIG. 5 and FIG. 5A is current-inventor's which a perspective view of one preferred LED night light or LED wall cover light inner circuit, LED(s) light source(s), USB ports, PCB, conductive wire, prong, transformer or invertor, and control system (here as the CDS photo cells) which install within the back base and front cover. This is one of the preferred embodiments.

From FIG. 5 the LED night light or LED wall cover light has base (50b) which has top hole (50h) and lower hole (50i) and top parts has compartment to allow install the USB Charger and LED(s) light on preferred anywhere of the said LED night light or LED wall cover light. The USB Charger has circuit (50q) which has its big PCB and small PCB (50p) to install transformer, resistor, capacitor, conductive wire, or related electric parts & accessories as (50q).

The current LED night light or LED wall cover light has 2 USB ports (50d2) also install on the circuit (50q) to allow to charge the other electric device from other electric device plug into the said 2 USB ports (50 d2).

The circuit (50q) also has the small PCB (50p) which has preferred SMT LEDs (SOL) install on and has the electric conductive wire (50w) to connect with circuit (50q) to offer the desire functions of lighting such as offer illumination or show the charging status such as while charging LED is show red color means "Lower power", show green color means "Charging now", Show Blue color "Fully Charged" . . . or has more colors to show (10%-30%-50%-75%-100% charging status) to let people the charging status by selected IC chip can get all kind of charging status indicator by the said multiple color LEDs or color changing LEDs while incorporate with selected IC chip.

Figure 5A:
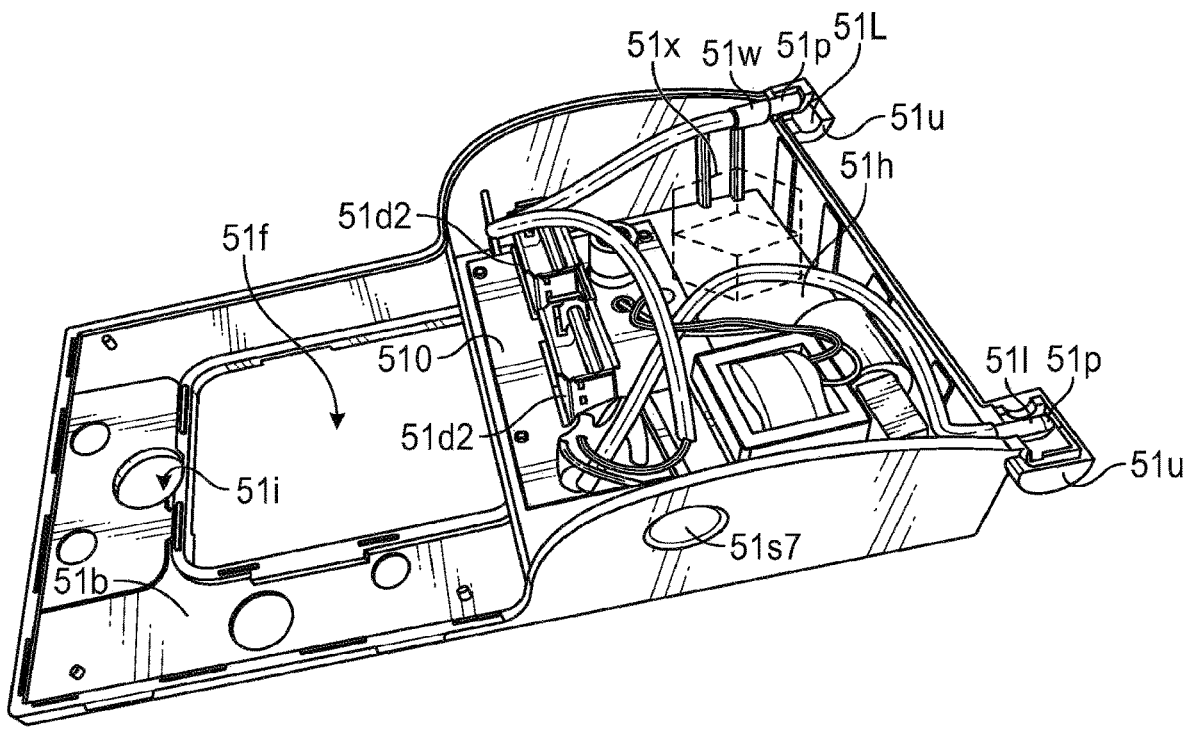
Figures 6, 6A, 6B:
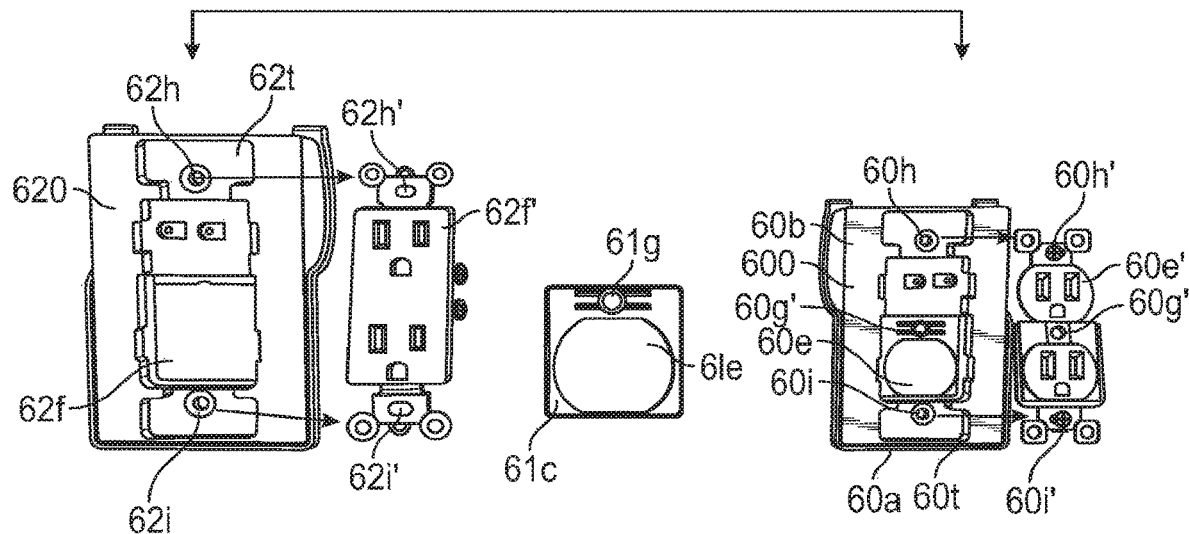
FIG. 6, 6A, 6B and FIG. 7, 7A, 7B show the relation with the moveable unit(s) or piece for the multiple function LED night light or LED wall cover light, wall existing inner receptacle for 2 different shape/construction/size for the current universal Multiple function LED night light or LED wall cover light.
Figures 7, 7A, 7B:
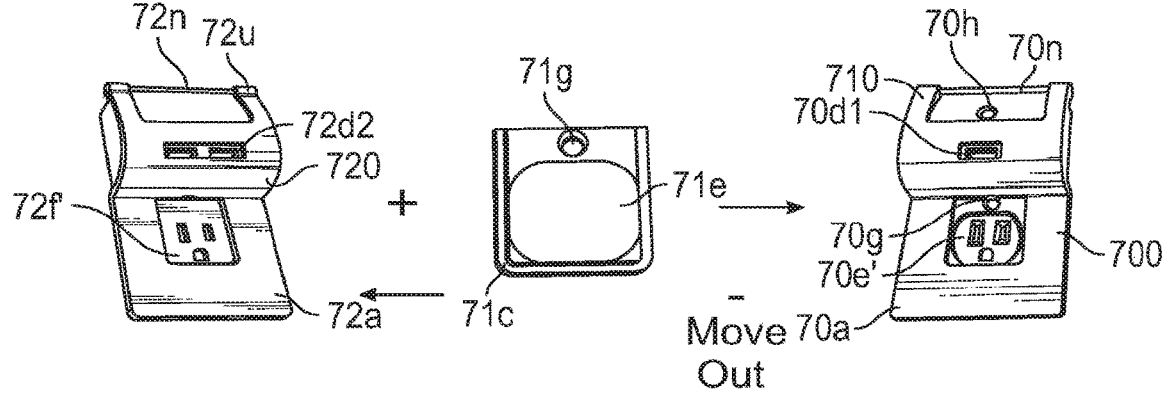
Figure 8:
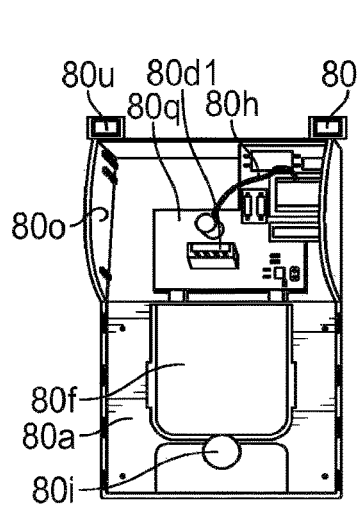
FIG. 8, 8A, 8B and FIG. 9, 9A, 9B show the 1 ports or 2 ports USB charger of Multiple functions LED night light or LED wall cover light which has the hinge type optics lens which has 2 ends to fit within the 2 half-groove(s) to make (1) light illumination or/and (2) Charging status or/and (3) cosmetic to cover the inner screw holes or or/and (4) fit within the other sensor, controller, wireless transmitting and receiving means, blue tooth receiver for wireless signal, remote control receiver, or wife related device to make the said more than two functions can add under this preferred optics lens for added Number 3 to Number N additional functions (N is any number).
Figure 8A:
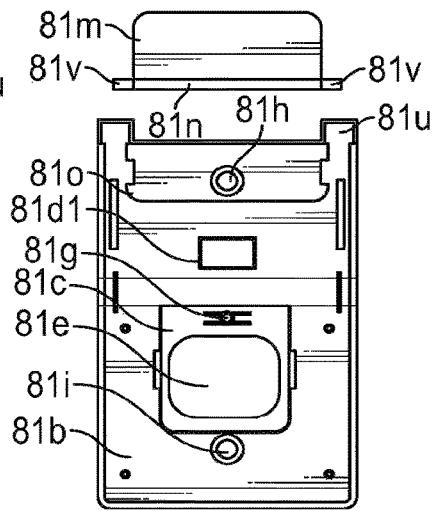
Figure 8B:
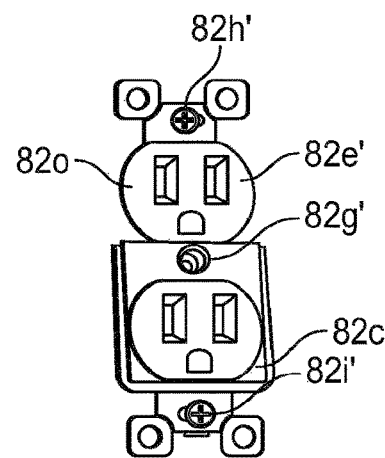

From FIG. 5A show more clear the other side for LED (51L) and small PCB (51p) and Wire (51W) and other controller (51x) which can offer Multiple function LED night light or LED wall cover light has more than two functions which the third functions is one of the optional outlets device, electric devices(s), LED light device, EL light device, Florescent tube device, power fail light device, illumination device, Wi-fi device, internet device, wireless router device, time piece, motion sensor device, Remote control device, Blue tooth device, wi-fi means, internet means, Video Camera device, Recording device, Memories means, digital data storage means, Power means, Energy saving means, Energy storage device, Batteries, DC Power means, conductive means, prong means, electric parts and accessories means. Optics means, reflective means, optics light traveling means to make the said LED night light or LED wall cover light has built-in more than two function which at least has one of USB charger and Light means.

Same as FIG. 5, the other controller (50X) for offer more than two function for the said LED night light or LED wall cover light.

From FIG. 5A the said built-in USB Charger or LED(s) light or other function can has desire controller which may selected from switch (S), Sensor (S1), Remote control (S2), Motion Sensor (S3), Blue tooth wireless transmitter or receiver (S4), Infra-Red remote control (S5), Wi-fi wireless controller (S6), Photo sensor (S7), CDS control (S8), or any other market available control means (S9) all still fall within the current invention scope of the claims to control the said multiple function LED night light or LED wall cover light has USB charger and light means in variety combination with other function as FIGS. 10,11,12,13,14,15,16,17, 18, 19, 20, 21, 22, 23 show all kind of combination still fall within the current invention scope and claims.

From FIG. 6, FIG. 6A, FIG. 6B and FIG. 7, FIG. 7A, FIG. 7B and FIG. 8, FIG. 8A, FIG. 8B and FIG. 9, FIG. 9A, FIG. 9B; All show the same details with above discussion so here do not discuss more details. From These drawing just show the different viewing angle for current invention features for front view, side view, inner circuit, wire arrangement, light means preferred arrangement, other controller system, other functions arrangement.

Figure 9:
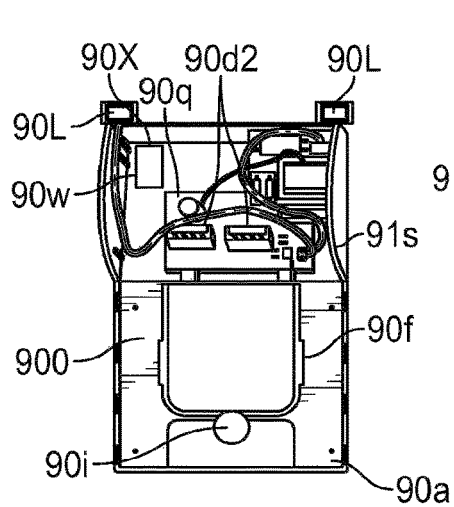
Figure 9A:
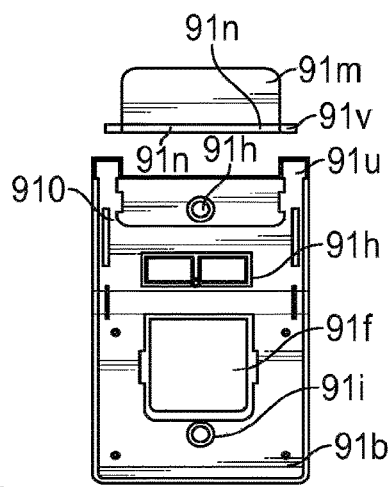
Figure 9B:
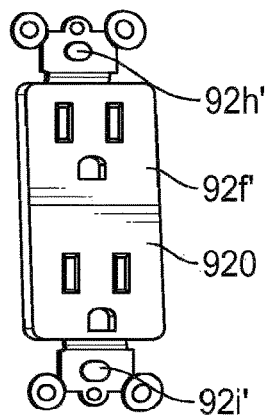
Figure 16:
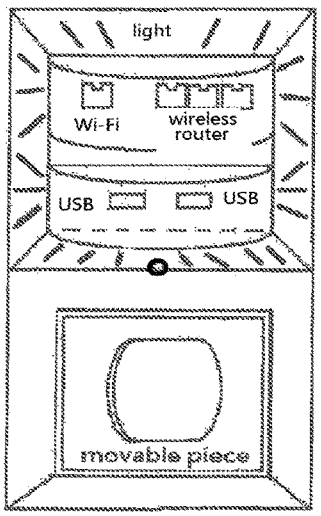
Figure 17:
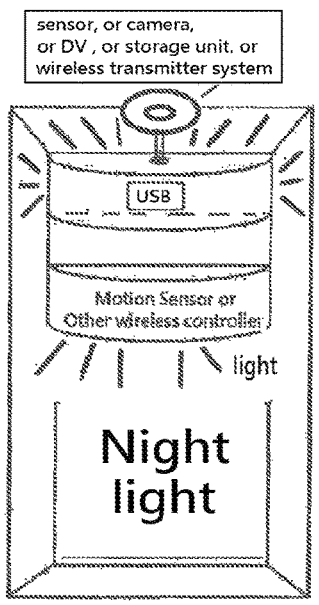
Figure 18:
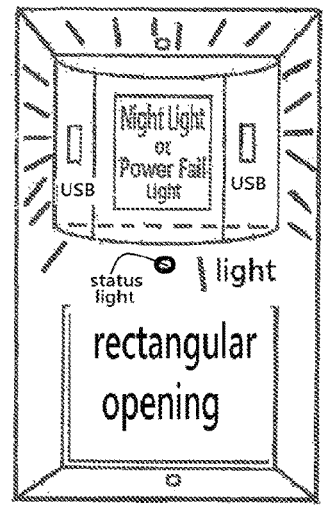
Figure 19:
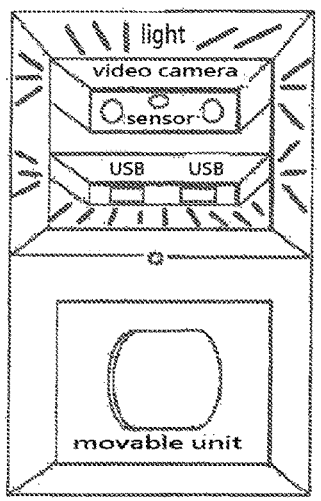

From FIGS. 8, 8A, 8B and FIGS. 9, 9A, 9B can see the USB Charging circuit and light means are fit within the front cover (81a)(91a) and back base (80b) (90b) and use clipper and sonic sealing to make the front cover and back base can sealed tight. The movable piece (81c) is fit on LED night light or LED wall cover light to make interchangeable from different inner receptacle (82e') and (92f). From FIGS. 8, 8A, 8B can see the oval-shape inner receptacle need the movable piece install on FIGS. 8, 8A, 8B LED night light or LED wall cover light so can fit well. From FIGS. 9, 9A, 9B show the rectangular shape inner receptacle no need movable piece because the front cover and back base already has the rectangular opening for fit rectangular inner receptacle.

The said FIGS. 9, 9A, 9B LED night light or LED wall cover light on current invention the front cover can be any shape with desired more functions than USB Charger and Built-in LED(s) light on anywhere of the said LED night light or LED wall cover light.

The above discussed are not intended to limit the scope of the current invention. All alternatives, variations, equivalent functions, and minor changes still fall within the scope of the current invention. For example, the number of prong can be at least one pair under some special requirements and still can supply power to two receptacles depending on the design of copper piece(s)/conductive unit(s), and the copper piece/conductive unit(s) also can be have any configuration as long as it supplies electricity as necessary. Furthermore, as described above, the LED(s) light may include any available LED(s) light and installation without departing from the scope of the current invention. The attachment kits, fastening kits, and installation kits also may be varied without departing from the scope of the invention.

The current invention for night light or cover light has following (18) features which basing on above discussion and all co-pending parent filed case(s) as below details;

1. A multiple-function plug-in LED light, comprising:
   at least one LED for at least one (A) illumination on desired area(s), optic-lens(es), window(s), hole(s) and (B) for status indication;
   at least one USB charger port for charging another product;
   at least one front cover and a back base, wherein;
   at least one prong supplies AC current to a built-in AC-to-DC circuit and supplies a DC current to the at least one USB charger and to at least one LED,
   wherein, at least one USB charger port receives an USB male plug arranged to deliver electrical current through a USB wire to another product,
   wherein, the plug-in LED light further includes at least one sensor(s), switch, CDS, photosensor, outlet(s), motion sensor, power fail sensor, Bluetooth connector, remote control device, brightness or color changing control circuit, and integrated circuit (IC).

2. A multiple-function plug-in LED light as discussed on 1, further comprising a movable piece adapted to enable the plug-in LED light to fit more than one type of plug-receiving wall receptacle.

3. A multiple-function plug-in LED light as discussed on 1, further comprising a wire arrangement structure for arranging and storing at least one of (1) wire connected to an AC outlet and (2) at least one separate wire connected between the at least one USB charger port and the at least one external electric or digital data device.

4. A multiple-function plug-in LED light as discussed on 1, wherein the LED plug-in light includes LEDs having different colors to provide color changing or color selecting lighting effects.

5. A multiple-function plug-in LED light as discussed on 1, wherein the LED plug-in light includes LEDs having different or pre-determined colors to indicate at least one (1) different charging status, or (2) status of surge system, or (3) status of power on-off, or (4) other protection system status.

6. A multiple-function plug-in LED light as discussed on 1, wherein said plug-in LED light has multiple USB ports supplied with said DC output current, and said DC output current is selected from 1.0 Amp, 2.1 Amp, 2.4 Amp, 3.1 Amp, 3.4 Amp, 4.2 Amp, 4.4 Amp, and more than 4.4 Amp; or from 12 Watt to 100 Watt.

7. A multiple-function plug-in LED light as discussed on 1, wherein an electrical conductor, said AC-to-DC circuit, and/or a DC-to-DC circuit connected to said at least one prong supplies power to said at least one (i) USB charger port, (ii) an LED circuit, and/or (iii) an additional function-providing device.

8. A multiple-function plug-in LED light as discussed on 1, further comprising a movable piece having (i) an oval shaped opening and (ii) at least one screw hole—for adapting the LED plug-in light to at least one electrical receptacle having an oval shape, wherein the movable piece is removed from the—night light in order to fit night light for an electrical receptacle having a rectangular shape.

9. A multiple-function plug-in LED light as discussed on 1, wherein the LED plug-in light has at least one additional function-providing device installed within the LED plug-in light, said additional function-providing device including at least one of an (1) electrical outlet, (2) electrical device, (3) second color LED, (4) power fail light device, (5) illumination device, (6) Wi-Fi device, (7) Internet device, (8) wireless router, (9) timepiece, (10) motion sensor, (11) remote control, (12) Bluetooth device, (13) video camera, (14) recording device, (15) digital data storage device, (16) power supply device, (17) time piece, (18) wireless router device, (19) motion sensor device, (20) memory device, (21) digital data storage device, (22) energy saving device, and (23) battery power bank device.

10. A multiple-function plug-in LED light, comprising:
  at least one LED light source;
  at least one prong arranged to be inserted into an AC wall outlet and supply power to an LED light source to for at least one pre-determined illumination selected from;
  (a) emit light through at least one of top, bottom, front, front window, front hole, side walls, edges, contour of the LED plug-in light, and
  (b) show a charging status;
    an AC-to-DC circuit that supplies a desired DC current to at least one USB port and the at least one LED light source,
    wherein the at least one USB port is arranged to receive a USB plug of an USB wire set to deliver electric current to at least one external electric or digital data device.

11. A multiple-function plug-in LED light as discussed on 10, further comprising an additional electrical device selected from:
  1. fragrance dispenser;
  2. lighting device;
  3. insect repelling device;
  4. timepiece;
  5. motion sensor;
  6. infrared sensor;
  7. Bluetooth electrical device controller;
  8. Wi-Fi device, router, or Internet device;
  9. video or audio device;
  10. wire arrangement device;
  11. a power fail light device;
    12. a power bank device; and
    13. a color changing, color selection,
    14. function selection, or brightness selection device.

12. An LED USB wall cover plate, comprising:
  at least one front cover and a back base assembled to form a housing of the USB wall cover plate, said USB wall cover plate having a shape corresponding to that of an existing wall plate,
  wherein the USB cover plate is fastened to an inner wall electrical receptacle by prongs extending through the back base, and includes a movable piece, said inner wall electrical receptacle having at least one AC outlet;
  at least one prong of the wall cover plate arranged to be inserted into the AC outlet to supply power to at least one AC-to-DC circuit and at least one LED light source installed within the USB wall cover plate to offer at least one (1) illumination, (2) a charging status, (3) surge or other protection indicator light (4) power on-off,
  wherein the USB wall cover plate further includes at least one additional built-in device selected from:
  1. a motion or photo sensor;
  2. a power fail device;
  3. a color or brightness selection or adjustment device;
  4. a power bank to charge other products while unplugged from a wall outlet;
  5. a switch;
  6. a wireless connection or controller device;
  7. an infrared or radio frequency remote control circuit;
  8. One of a Bluetooth, Z-way, ZigBee, Wi-Fi, or Internet connection device;
  9. downloaded app software; and
  10. a moveable piece that is added-on the wall cover plate to fit oval or rectangular receptacles.
  11. A multiple function LED night light, comprising;
13. At least one LED offer illumination shown on night light housing, window(s), hole(s), optic-lens(s).
  AT least one outlet(s) built-in night light.
  At least one AC-to-DC circuit to change AC power source to pre-determined DC circuit connect with at least one circuit, IC, photo sensor, motion sensor, dimmer switch for LED light function(s) and light effect(s).

14. A multiple function(s) LED night light as discussed on 13, further incorporate with surge or other safety protection system.

15. A multiple function(s) LED night light as discussed on 13, further incorporate with LED(s) to show the surge protection system status.

16. A multiple function(s) LED night light as discussed on 13, further incorporate with USB charger system with USB output port(s).

17. A multiple function(s) LED night light as discussed on 13, further incorporate with the LED(s) has pre-determined number of color(s), number of LED(s).

18. A multiple function(s) LED night light as discussed on 13, further incorporate with LED(s) for different or multiple color(s) to shown charging status.

I claim:

1. A multiple function plug-in LED light, comprising:
  at least one LED for providing at least one of:
  (A) illumination of at least one desired area, optics lens, window, or hole;
  (B) illumination for at least one of the following status indications: (b-1) charging status indication by a multiple color LED to indicate low charge, currently charging, and fully charged statuses, (b-2) on or off surge protection system status, and (b-3) switch position;
  at least one USB charger port for charging another product;
  at least one front cover and a back base; and
  at least one prong for supplying AC current to a built-in AC-to-DC circuit that supplies a DC current to the at least one USB charger port and the at least one LED,
  wherein the at least one USB charger port is configured to receive a USB male plug of an external USB wire for delivering electrical current to the another product, and
  the plug-in LED light further includes at least one of a sensor, switch, CDS, photosensor, outlet, motion sensor, power fail sensor, Bluetooth connector, remote control device, brightness or color changing control circuit, and integrated circuit (IC).

2. A multiple function plug-in LED light as claimed in claim 1, further comprising a movable piece adapted to enable the plug-in LED light to fit more than one type of plug-receiving wall receptacle.

3. A multiple-function plug-in LED light as claimed in claim 1, further comprising a wire arrangement structure for arranging and storing at least one of (1) a wire connected to an AC outlet and (2) at least one separate wire connected between the at least one USB charger port and the at least one external electric or digital data device.

4. A multiple-function plug-in LED light as claimed in claim 1, wherein the LED plug-in light includes a plurality of LEDs having different color chips or dice and built into one LED to provide color changing or color selecting lighting effects.

5. A multiple-function plug-in LED light as claimed in claim 1, wherein the LED plug-in light includes LEDs having different or predetermined colors to indicate at least one of: (1) a different charging status, (2) a surge system status, (3) a power on-off status, and (4) another protection system status.

6. A multiple-function plug-in LED light as claimed in claim 1, wherein said plug-in LED light has multiple USB ports supplied with said DC output current, and said DC output current is selected from 1.0 Amp, 2.1 Amp, 2.4 Amp, 3.1 Amp, 3.4 Amp, 4.2 Amp, 4.4 Amp, and more than 4.4 Amp; or from a DC output current having an output power of from 6 Watt to 100 Watt.

7. A multiple-function plug-in LED light as claimed in claim 1, wherein at least one of an electrical conductor, said AC-to-DC circuit, and a DC-to-DC circuit connected to said at least one prong supplies power to said at least one of (i) the USB charger port, (ii) an LED circuit, and/or (iii) an additional function-providing device.

8. A multiple-function plug-in LED light as claimed in claim 1, further comprising a movable piece having (i) an oval shaped opening and (ii) at least one screw hole for adapting the LED plug-in light to at least one electrical receptacle having an oval shape, wherein the movable piece is removed from the plug-in LED light in order to fit an electrical receptacle having a rectangular shape.

9. A multiple-function plug-in LED light as claimed in claim 1, wherein the LED plug-in light has at least one additional function-providing device installed within the LED plug-in light, said additional function-providing device including at least one of an (1) electrical outlet, (2) electrical device, (3) second color LED, (4) power fail light device, (5) illumination device, (6) Wi-Fi device, (7) Internet device, (8) wireless router, (9) timepiece, (10) motion sensor, (11) remote control, (12) Bluetooth device, (13) video camera, (14) recording device, (15) digital data storage device, (16) power supply device, (17) timepiece, (18) wireless router device, (19) motion sensor device, (20) memory device, (21) digital data storage device, (22) energy saving device, and (23) battery power bank device.

10. A multiple-function plug-in LED light, comprising:
at least one LED light source;
at least one prong arranged to be inserted into an AC wall outlet and connected with at least one of an AC-to-DC circuit and a DC-to-DC circuit, and a manual switch or photosensor, to operate at least one LED, wherein the at least one LED light source emits light beams for steady area illumination through at least one of a (1) side lens, (2) bottom lens, (3) front lens, (4) front window, (5) front hole, (6) side wall, (7) edges, and (8) contour of the LED light, and
at least one female AC receiving port built in the LED light to receive a plug-in male AC plug or AC prong to supply AC power to other AC products.

11. A multiple-function plug-in LED light as claimed in claim 10, further comprising at least one of the following additional electrical functions or devices:
a. a fragrance dispenser;
b. a smell device;
c. an insect repelling device;
d. a timepiece;
e. a motion sensor;
f. an infrared sensor;
g. a Bluetooth electrical device controller;
h. a Wi-Fi device, router, or Internet device;
i. a video or audio device;
j. a wire arrangement device;
k. a power fail light device;
l. a power bank device; and
m. color changing and/or selection of colors for charging status indication;
n. dimmer function and/or brightness selection; and
o. at least one USB charging port and a built-in AC-to-DC circuit to change input AC power to DC power to drive at least one of a (a) circuit, (b) IC, (c) DC-to-DC circuit, (e) IC control switch, (f) slide switch, (g) sensor, (h) radar sensor, (i) dimmer switch, (j) variable resistor or switch, (k) color changing and/or selection IC or switch, (l) charging status detector circuit, and (m) charging power detector device.

12. An LED USB wall cover plate, comprising:
at least one front cover and a back base assembled to form a housing of the USB wall cover plate which overlays and covers an existing wall cover;
at least one built-in prong to insert into at least one female outlet receiving port of an inner wall electrical receptacle;
at least one LED light source; and
at least one of:
(i) an AC-to-DC and/or DC-to-DC circuit,
(ii) an IC controlling at least one LED for color functions and/or charging status detection,
(iii) a photosensor, motion sensor, radar sensor, or power fail detector;
wherein the LED USB wall cover plate includes or offers USB charging functions and at least one of:
(1) an area, side, contour, or surface having illumination functions or performances selected from:
(a) fixed color, color changing, or color mixing display function or a single piece, multiple-color LED,
(b) color or brightness setting, adjusting, changing, or selection,
(c) sequential light effects, and
(d) flashing,
(2) at least one fixed color, color changing, or color mixing charging indicator function,
(3) at least one surge or protection function, and
(4) a timer, predetermined period time circuit, or IC, to turn-on or turn-off power or illumination,
(5) a power bank function to charge other products while unplugged from a wall outlet,
(6) a switch,
(7) a wireless connection or controller device,
(8) an infrared or radio frequency remote control circuit,
(9) one of a Bluetooth, Z-way, ZigBee, Wi-Fi, or Internet connection device,
(10) downloaded app software, and (11) a moveable piece that is added-on and removable from the wall cover plate to fit oval or rectangular receptacles.

13. A multiple function LED night light, comprising:
at least one LED arranged to provide single color area illumination from at least one housing, window, hole, or optic lens;
at least one outlet built into the LED night light to supply AC power to another device when a male AC prong of the another device is inserted into the at least one outlet;
at least one USB charging system built-in the LED night light to charge external products through external USB wires; and
at least one AC-to-DC circuit for changing AC power from an AC power source into a DC power for supply to an least one of a control circuit, photosensor, motion sensor, radar sensor, power fail detector, DC-to-DC circuit, and dimmer switch, for controlling the at least one LED to provide LED light functions or effects.

14. A multiple function LED night light as claim 13, further including a surge or other safety protection system.

15. A multiple function LED night light as claim 13, further including at least one LED to show a surge protection system status or a charging status.

16. A multiple function LED night light as claim 13, further including a USB charger system with at least one USB output port.

17. A multiple function LED night light as claim 13, wherein the at least one LED is a one color LED.

18. A multiple function LED night light as claim 13, further including at least one status LED having a plurality of built-in different color dice or chips to show charging status.

* * * * *